United States Patent [19]

Kramer et al.

[11] Patent Number: 5,746,774
[45] Date of Patent: May 5, 1998

[54] KNEE JOINT MECHANISM FOR KNEE DISARTICULATION PROSTHESIS

[75] Inventors: Steven Kramer, Perrysburg; Sujatha Srinivasan, Mount Sterling; Verner Swanson, Toledo, all of Ohio

[73] Assignee: The University of Toledo, Toledo, Ohio

[21] Appl. No.: 587,129

[22] Filed: Jan. 16, 1996

Related U.S. Application Data

[63] Continuation of Ser. No. 303,502, Sep. 9, 1994, abandoned.

[51] Int. Cl.$^6$ .................................................... A61F 2/64
[52] U.S. Cl. .................................................... 623/39; 623/44
[58] Field of Search .......................... 623/39–44, 45, 623/46

[56] References Cited

U.S. PATENT DOCUMENTS

| | | | |
|---|---|---|---|
| 3,823,424 | 6/1974 | May | 623/39 |
| 3,901,223 | 8/1975 | May | 623/39 |
| 4,310,932 | 1/1982 | Näder et al. | 623/39 |
| 4,911,709 | 3/1990 | Marlow et al. | 623/43 |
| 5,171,325 | 12/1992 | Aulie | 623/39 |
| 5,253,189 | 10/1993 | Kramer | 364/578 |
| 5,376,137 | 12/1994 | Shorter et al. | 623/44 |

FOREIGN PATENT DOCUMENTS

| | | | |
|---|---|---|---|
| 1779362 | 12/1992 | U.S.S.R. | 623/39 |
| 1418496 | 12/1975 | United Kingdom | 623/39 |
| 1533796 | 11/1978 | United Kingdom | 623/39 |
| 2134392 | 8/1984 | United Kingdom | 623/39 |

OTHER PUBLICATIONS

Blatchford Endolite High Technology Prosthesis Catalog, 1992, AFI Endolite, Hialeah, Florida.

Freudenstein, F. and Woo, L.S.,1969, "Kinematics of the Human Knee Joint," Bulletin of Mathematical Biophysics, vol. 31, pp. 215–232.

Hobson, D.A. and Torfason, L.E.,1974, "Optimization of Four–Bar Knee Mechanisms—A computerized Approach", Journal of Biomechanics, vol. 7, pp. 371–376.

Hosmer Dorrance Corporation, 1987, Ultra Roelite Knee Catalog, Campbell, CA.

Kegel, Bernice & Byers, James L., 1977, "amputee's Manual . . . mauch s–n–s–nee", Medic Publishing Co., Bellevue, WA.

Lowe, P.J., 1974, "Stance Phase Control of an Above–Knee Prosthesis," Human Locomotor Engineering, pp. 98–102, The Institution of Mechanical Engineers, London.

Mauch Laboratories, Inc., 1976, Manual for the Henschke-–Mauch SNS Hydraulic System. Dayton, Ohio.

Mauch Laboratories, Inc. 1988, Technical Bulletin of the USMC–Mauch Polycentric Knee, Dayton, Ohio.

Patil, K.M. and Chakraborty, J.K., 1991, "Analysis of a New Polycentric Above–Knee Prosthesis with a Pneumatic Swing–Phase Control", Journal of Biomechanics, vol. 24, No. 3/4, pp. 223–233.

Swanson, V., 1992, "Moving Ahead", A publication of Swanson Orthotic and Prosthetic Center, Toledo, No. 14.

*Primary Examiner*—John G. Weiss
*Assistant Examiner*—Bruce E. Snow
*Attorney, Agent, or Firm*—Brinks Hofer Gilson & Lione

[57] ABSTRACT

An improved four-bar knee joint mechanism for use in knee disarticulation prosthesis is shown, including a coupler link forming a negative angle with the horizontal when said knee joint mechanism is in its stance position, an anterior link, a fixed link in a horizontal position when said knee joint is in the extended or stance position, and a posterior link, the dimensions of the links and the angle the coupler link makes with the horizontal being chosen to optimize the instant center of the mechanism.

24 Claims, 16 Drawing Sheets

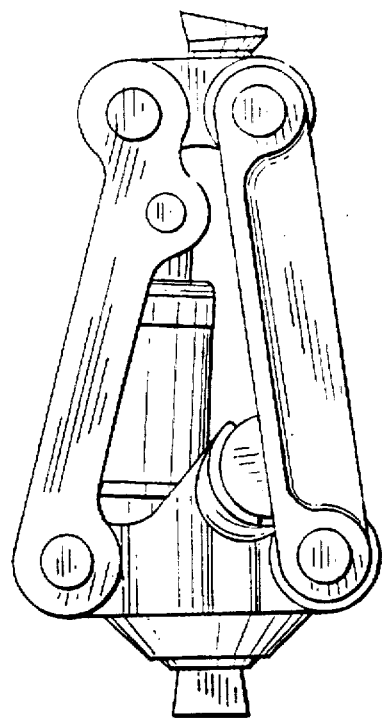
FIG. 1
(PRIOR ART)
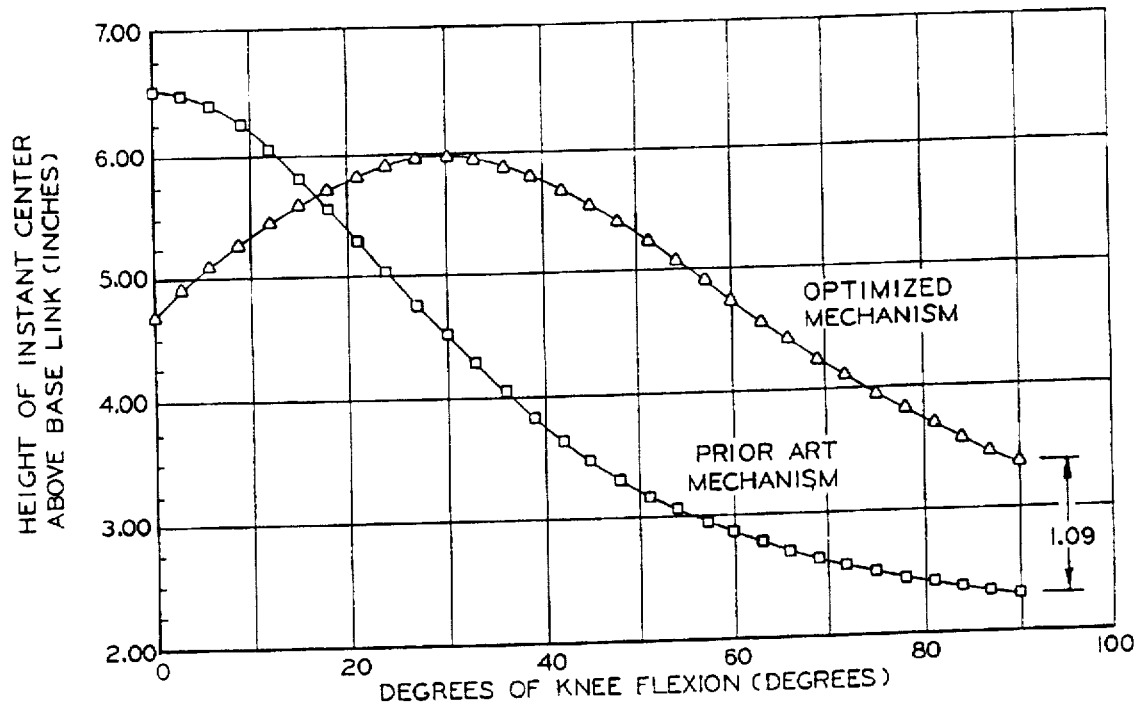
FIG. 2.7

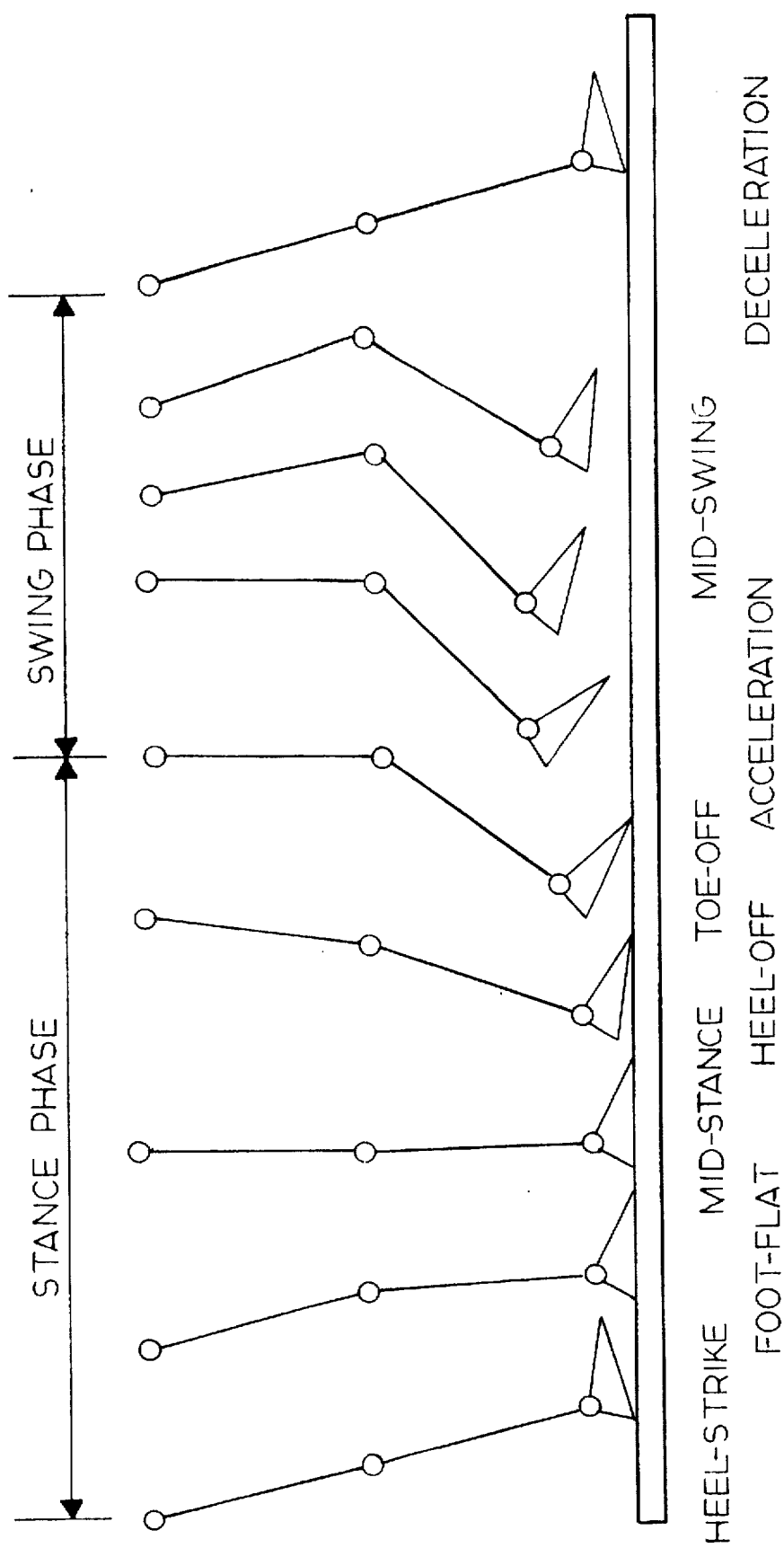
FIG. 1.1

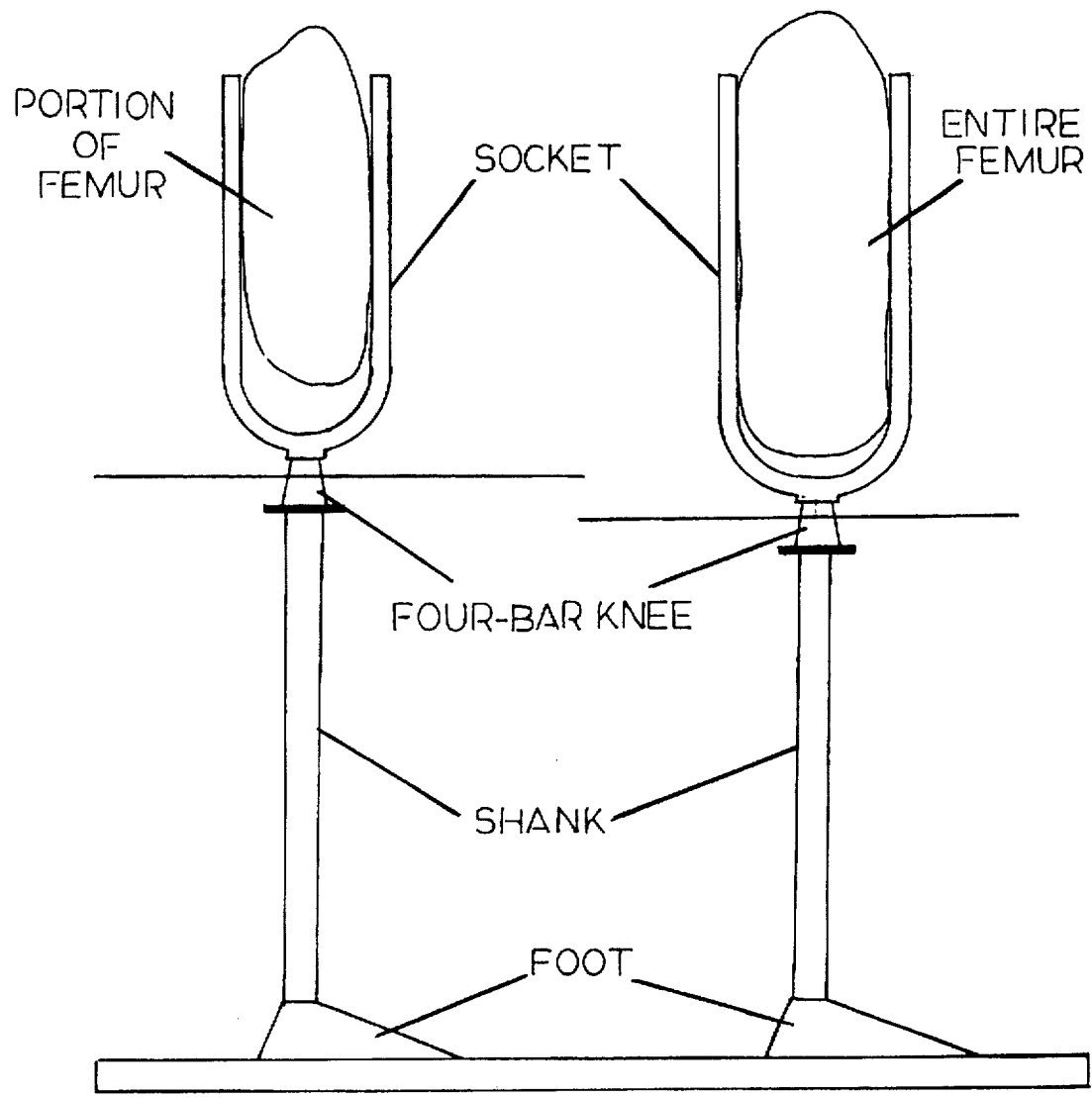
FIG. 1.2

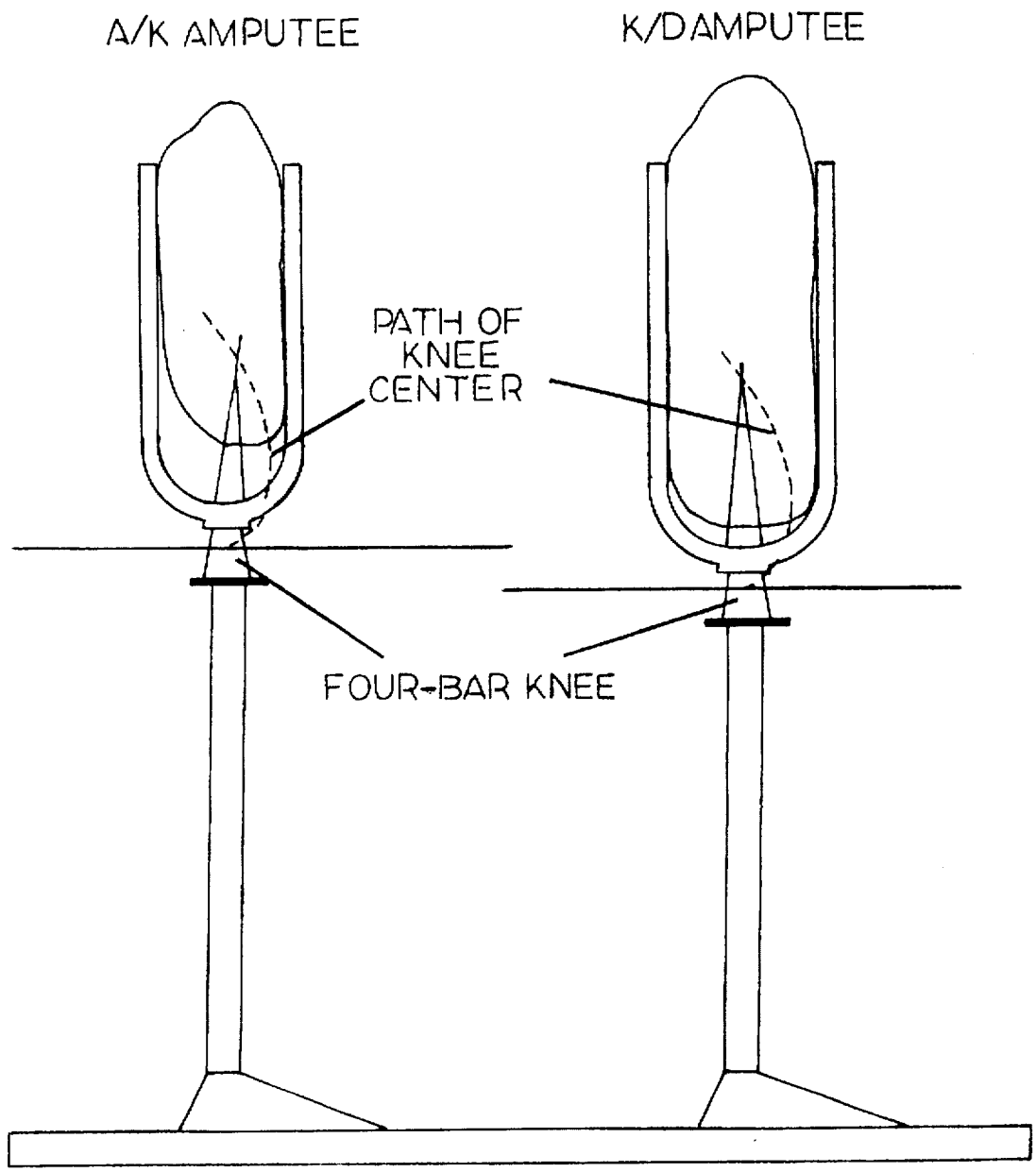
FIG. 1.3

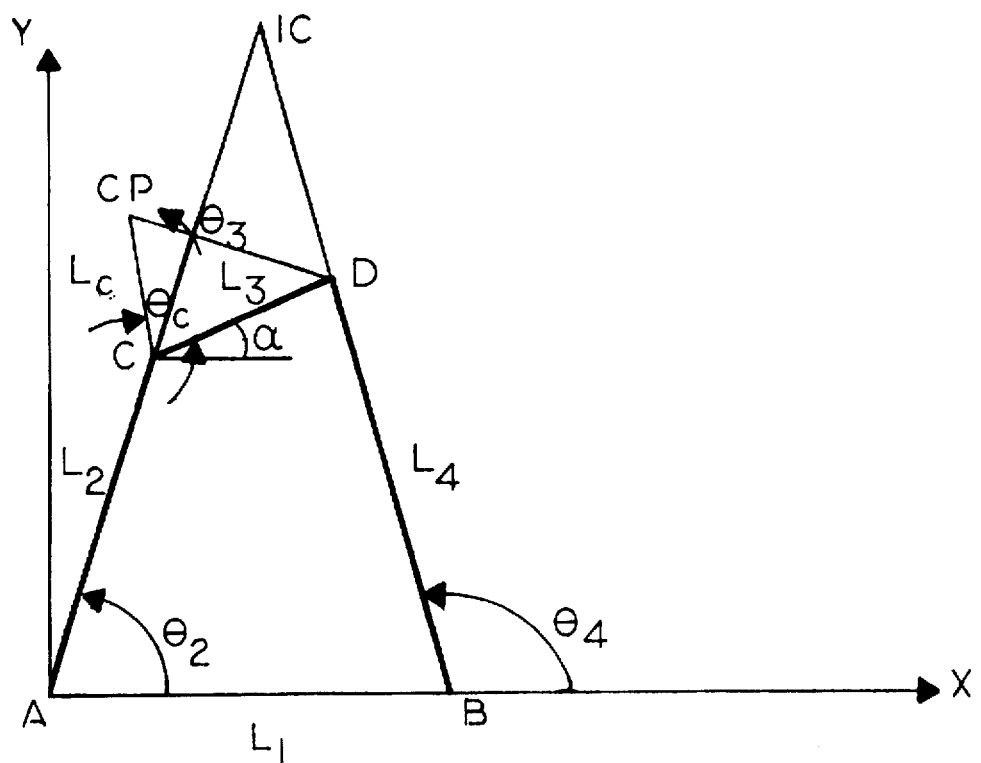
FIG. 1.4

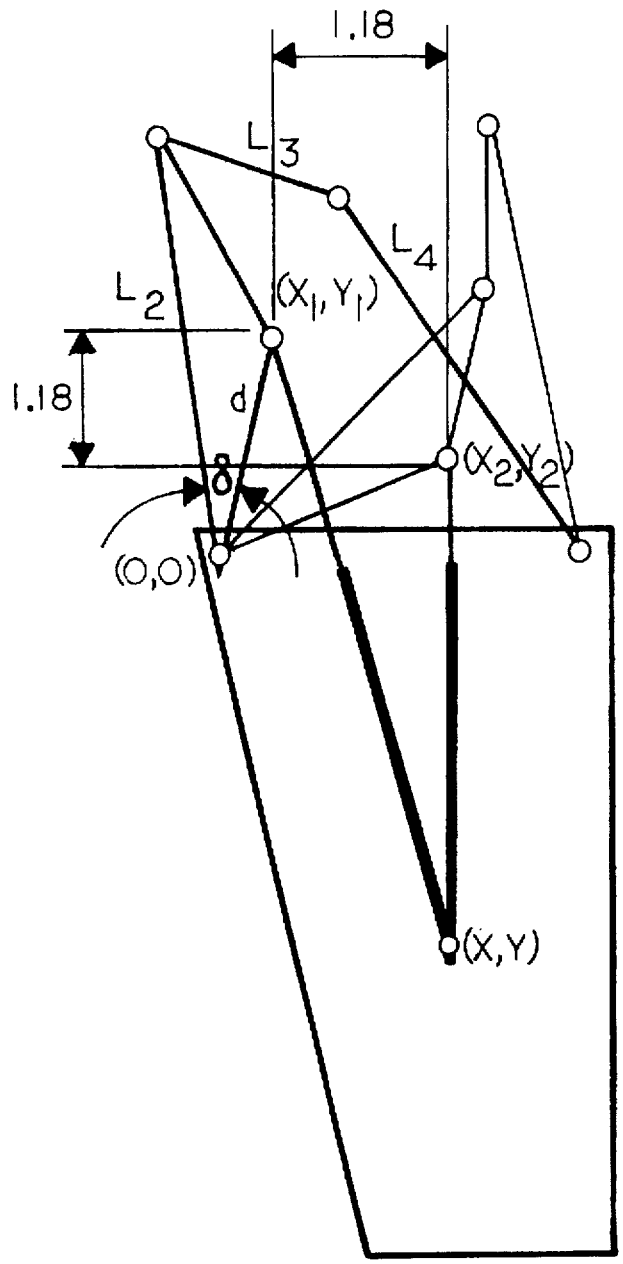
FIG 1.5

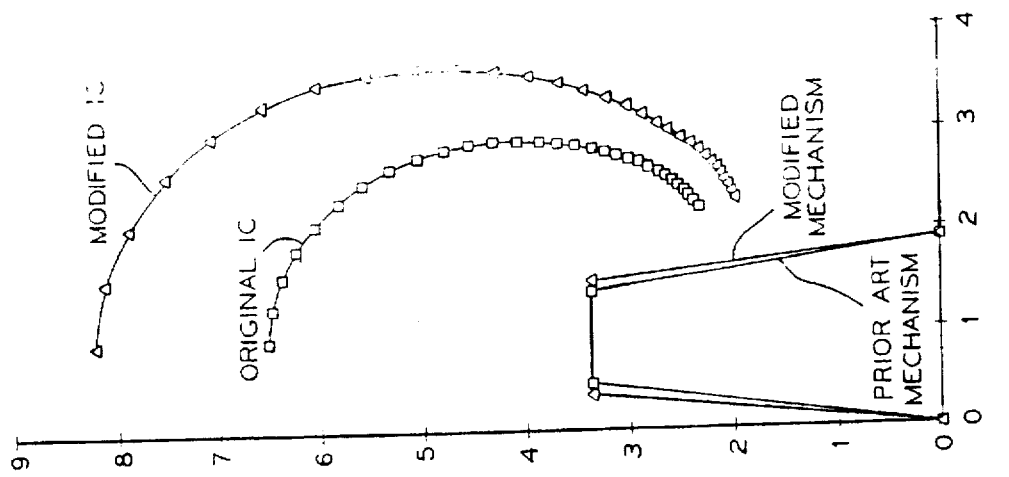
FIG. 2.3
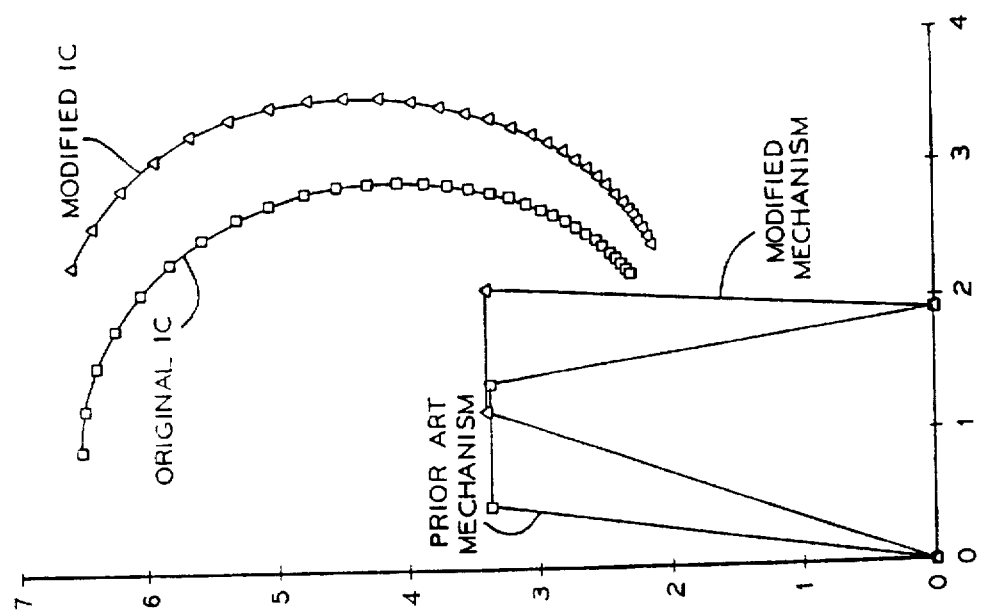
FIG. 2.2
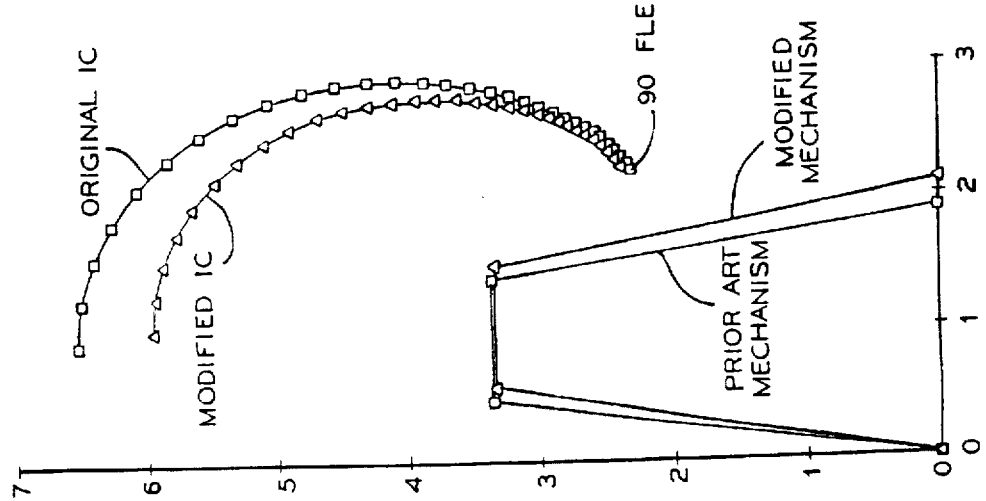
FIG. 2.1

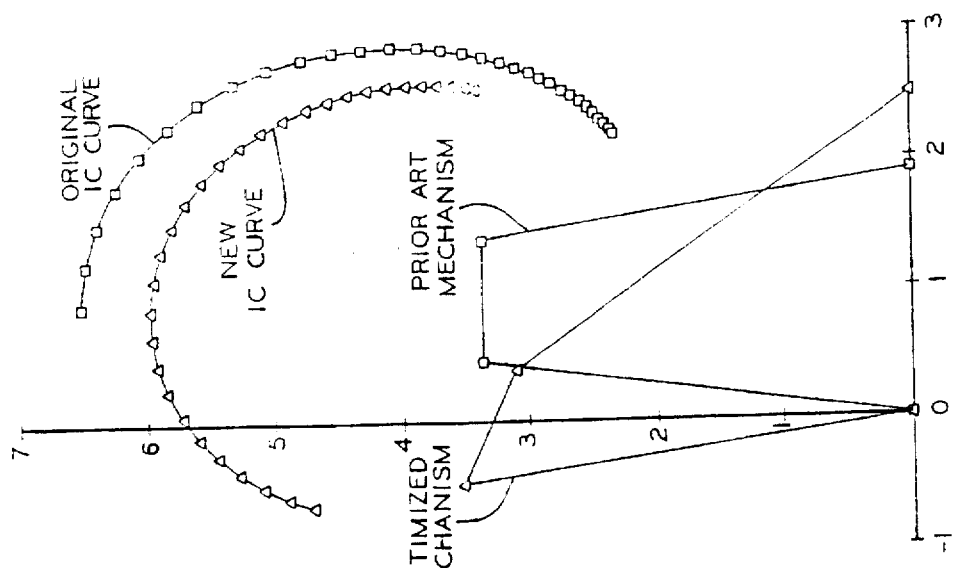
FIG. 2.6
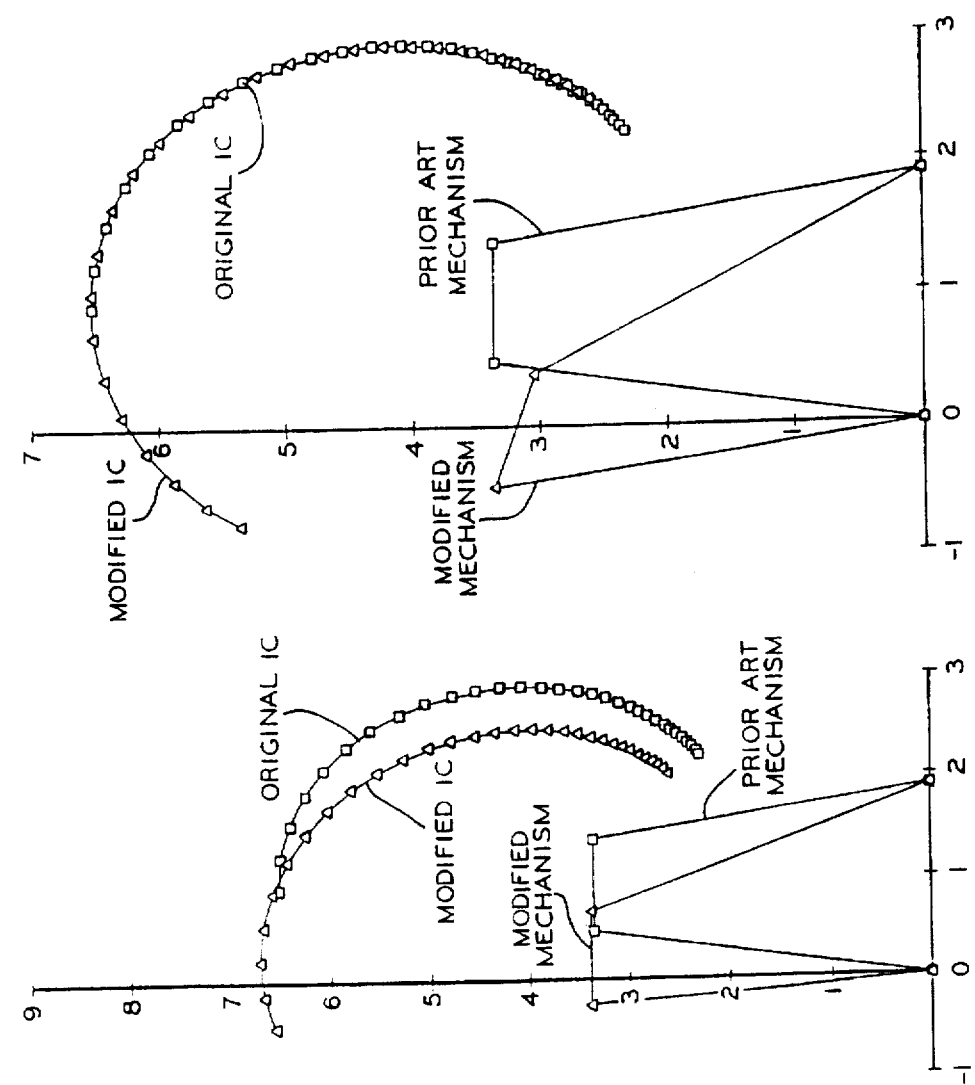
FIG. 2.5
FIG. 2.4

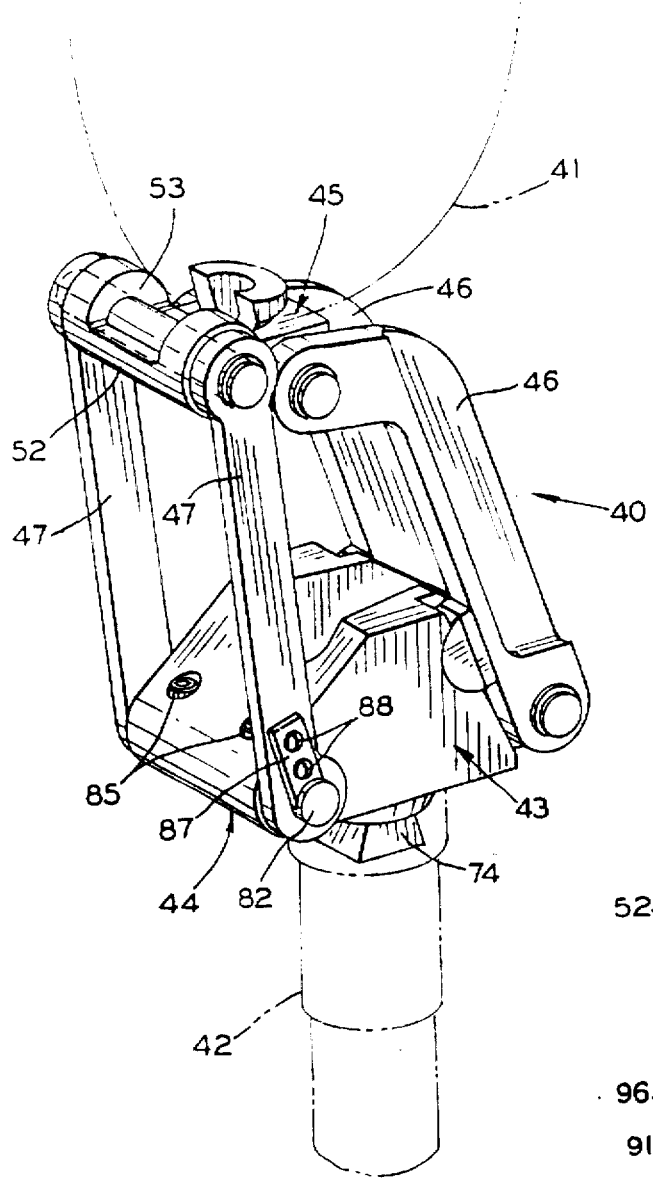
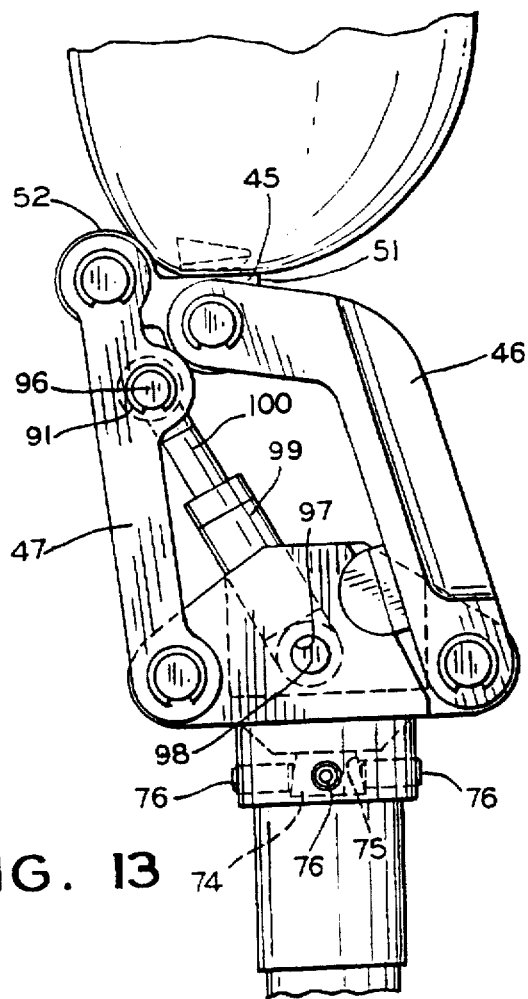
FIG. 3
FIG. 13

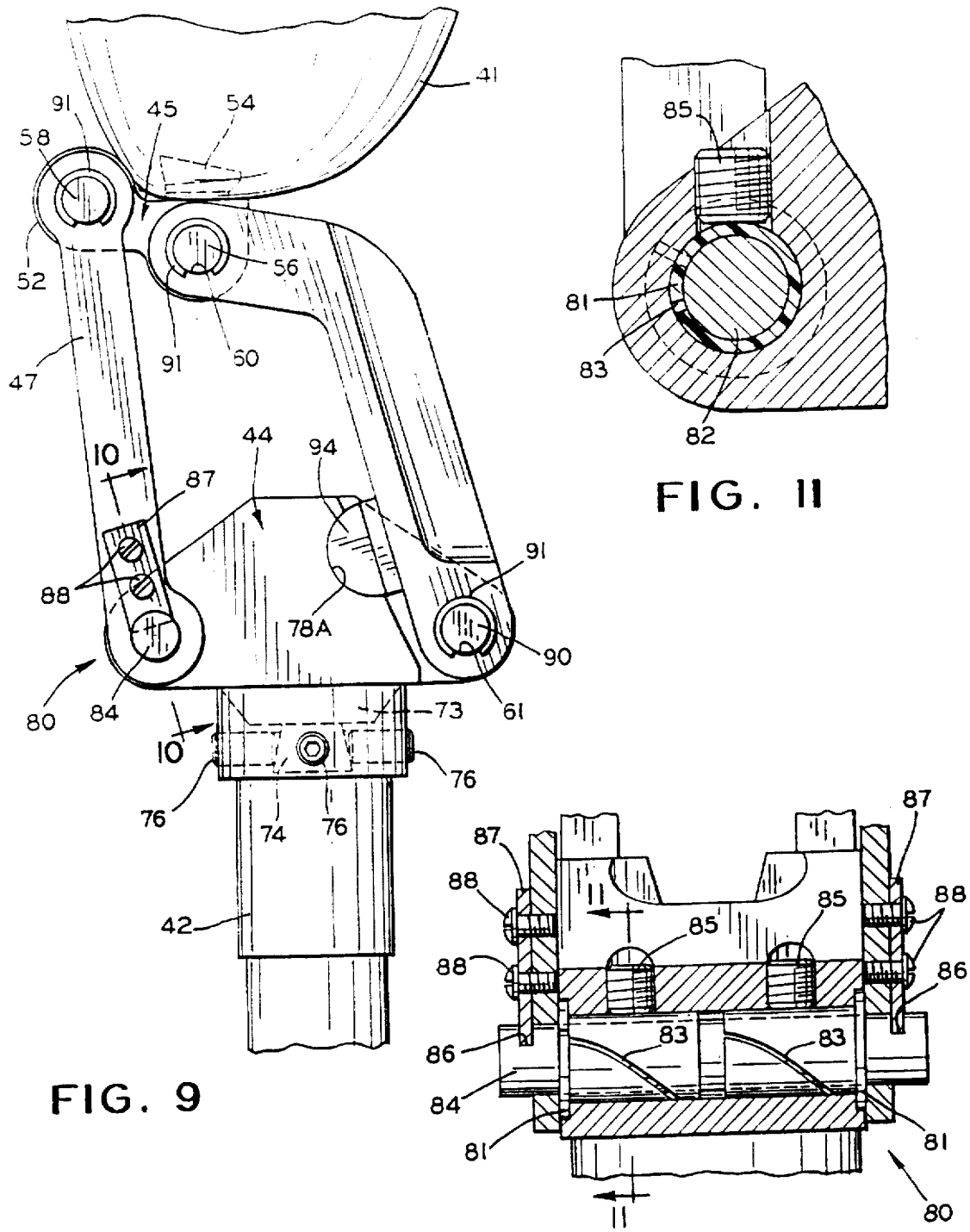

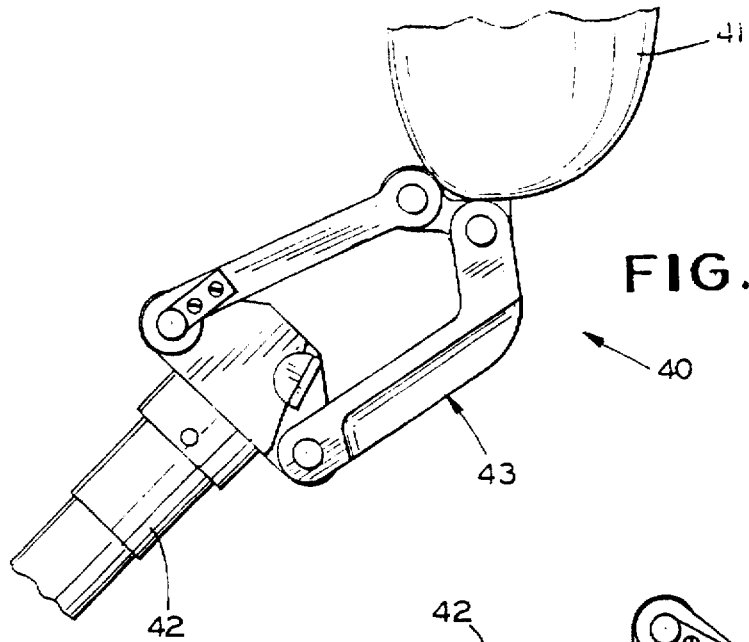
FIG. 12.1
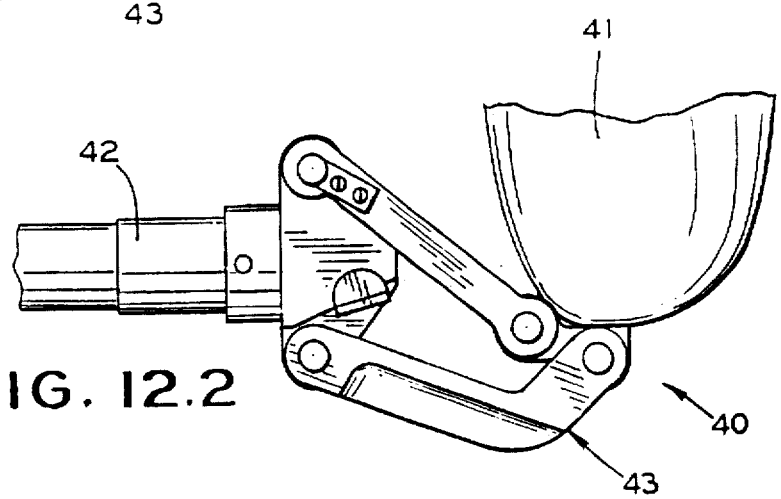
FIG. 12.2
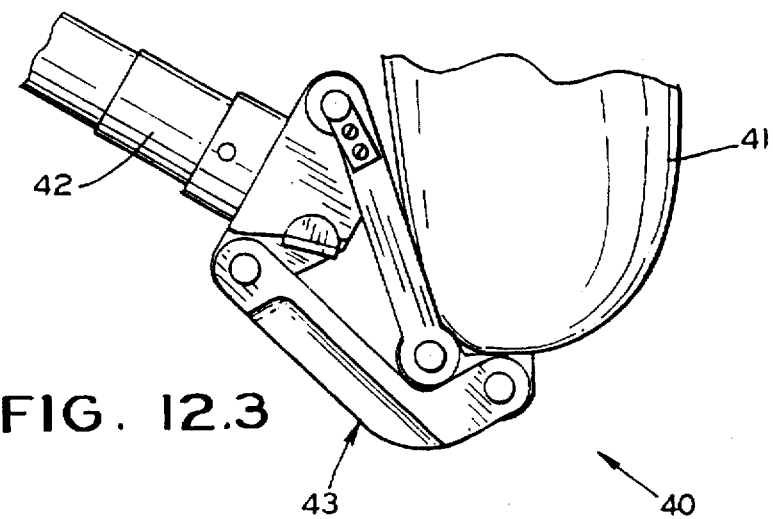
FIG. 12.3

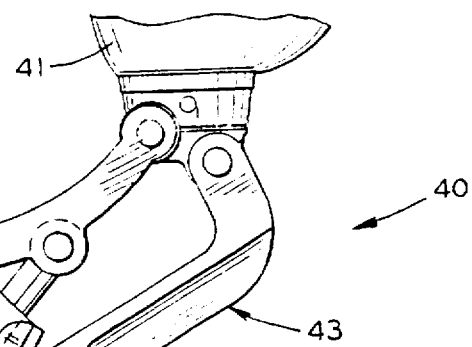
FIG. 16.1
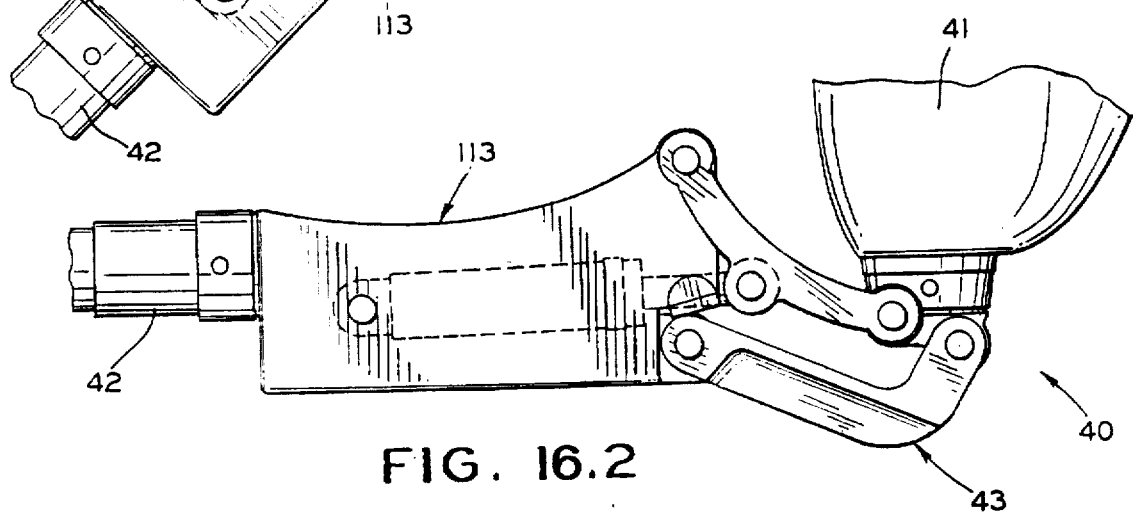
FIG. 16.2
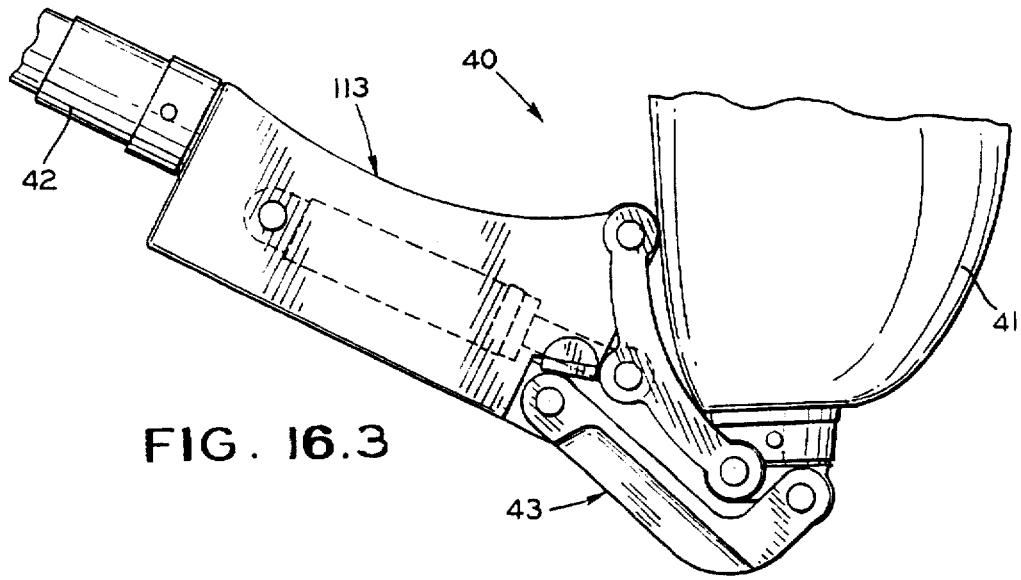
FIG. 16.3

KNEE JOINT MECHANISM FOR KNEE DISARTICULATION PROSTHESIS

This application is a continuation of application Ser. No. 08/303,502 filed on Sep. 9, 1994 now abandoned.

BACKGROUND OF THE INVENTION

1. Field of the Invention

The present invention relates in general to knee joint mechanisms for use in prostheses. More particularly, the present invention relates to an improved knee joint mechanism for use in a knee disarticulation prosthesis. Most particularly, the present invention relates to an improved four bar knee joint mechanism for use in a knee disarticulation prostheses wherein the dimensions of the links or bars and their position are chosen to optimize the height of the instant center of the mechanism above the normal knee joint.

2. Description of the Prior Art

Mechanical substitutes (prosthesis) for human lower limbs have advanced from small tree trunks shaped into peg legs in ancient times to today's sophisticated prosthesis with controlled motion. Understanding normal human walking provides the basis for the design and development of all of these mechanical substitutes.

Normal human locomotion has been described as a series of rhythmical alternating movements of the limbs and trunk which result in the forward progression of the body's center of gravity.

One gait cycle as shown in FIG. 1.1 below consists of the activity that occurs between heel strike of one limb and the subsequent heel strike on the same side. During a single gait cycle each limb passes through one stance or extended phase and one swing phase. The stance or extended phase begins at the instant the heel touches the floor (heel strike). Shortly thereafter, the sole makes contact with the ground (foot-flat). Next the body weight is swung directly over the supporting extremity and continues to rotate over the foot (mid-stance). As the body mass above the ankle continues to rotate forward, the heel lifts off the ground (heel-off). Shortly after this, the body is propelled forward by the forceful action of the calf muscles (push-off). The push-off phase terminates when the entire foot rises from the ground (toe-off).

The anatomical position is the upright position, therefore flexion is a movement of the body part away from the extended or stance or anatomical position. Thus, bending of the knee is knee flexion, extension is a movement of a limb towards the anatomical position, thus knee extension is a movement in the "straightening" direction.

The design configuration of the prosthesis will effect the degree of voluntary control required by the amputee in the various phases of the walking cycle. The main requirement in the replacement of the lower extremity is to design a device which has the external shape and appearance of a normal leg and which permits the amputee to walk comfortably and safely without undue mental or physical effort.

In level walking the normal human knee rotates through a range of approximately 70° going from a position of full extension in early and mid stance to 70° of flexion shortly after toe-off.

In normal human locomotion, flexion of the knee is one of the factors that smoothens out the path of the center of gravity of the body, thereby keeping the energy expenditure at a minimum. Thus, a prosthetic knee should allow flexion while compensating for the loss of muscle control both with regard to stability and swing control. Therefore, in designing a knee joint for a prosthesis, it is desirable to approximate the position and motion of the natural knee joint as closely as possible. Information on the motion of the natural knee joint is available to those skilled in the art through the work of F. Freudenstein and L. S. Woo in the article *Kinematics of the Human Knee Joint*, published in the Bulletin of Mathematical Biophysics, Volume 31, 1969.

In the case of above-knee (A/K) amputees, numerous models for artificial knee joints for prostheses have been designed and developed so far. The development of the knee joints for A/K amputees has progressed far ahead of the development of knee joints or prostheses for knee disarticulation or K/D amputees because with A/K amputees the knee joint can be placed in approximately the position of the anatomical knee. Thus, there are available single axis knee joints or polycentric devices for A/K amputees which, when positioned on the prosthesis for such amputees, is in the position of a normal knee joint, and in which knee motion approximates closely the motion of the natural knee. Such knees are known as polycentric knees or physiological knees.

However when such joints must be used in the case of a K/D amputee, where the amputation is through the knee joint, this similarity to the normal knee action is destroyed. The stump is the longest in the case of a K/D amputee. Consequently when a prosthesis similar to that for an A/K amputee is used, the knee joint drops to a level lower than that of the normal knee joint. This difference is generally about 1.5 to 3.0 inches, and causes significant problems in gait because of the toe of the prosthesis striking the ground, especially if the amputee has one normal limb. Therefore a problem has been presented to those skilled in the art as to how to regain the normal knee action in a knee disarticulation prosthesis.

Considerable emphasis has been placed on the search for a suitable knee joint mechanism for a K/D prosthesis because of the substantial benefits of through-knee amputations. Orthopedic surgeons perform through-knee amputations whenever they can because this has a distinct advantage over an amputation above the knee. A through-knee amputation preserves the condyles of the femur, and this improves the strength of the residual limb by virtue of retention of the larger weight-bearing surfaces. In addition, the longer stump with muscles of the femur intact provide better leverage and hence better control of the prosthesis the amputee uses. In the case of children, it is especially significant because amputation above the knee prevents further bone growth. Hence, a suitable knee mechanism for K/D amputees would be beneficial to a large number of patients. However, the problem of how to regain normal knee action with a knee mechanism placed below the level of the normal knee has proved to be a significant problem in the art.

Thus, those skilled in art of prosthesis have continued to search for a solution to the problem of how to provide a knee joint mechanism for K/D prothesis. Their search has resulted in the development of an improved four-bar knee joint mechanism for use in K/D prothesis which gives significantly improved performance.

SUMMARY OF THE INVENTION

An improved four-bar knee joint mechanism for use in knee disarticulation prostheses is provided, including a coupler link or links forming a negative angle with the horizontal when said knee joint mechanism is in its stance or extended position, an anterior link or links, a fixed link or links in a horizontal position when said knee joint mechanism is in the extended or stance position, and a posterior link or links.

For ease of explanation, the singular term "link" will sometimes be used hereinafter to describe the various links of the four-bar mechanism, although it can be easily understood by one skilled in the art that more than one link may form, any portion of the four-bar mechanism.

The dimensions of the coupler link, the anterior link, the fixed link, and the posterior link as well as the angle made by the coupler link with the horizontal, are chosen to optimize the height of the instant center of the mechanism. This results when the mechanism is mounted in a prosthesis, in that prosthesis having an instant center as far as possible above the normal knee joint.

In one embodiment of the invention, the dimensions of the links of the four-bar mechanism, as well as the angle the coupler link makes with the horizontal, are chosen such that the instant center of the knee joint, when mounted in a prosthesis, will be above the level of the normal knee joint for up to 90° flexion.

In another embodiment of the invention, the dimensions of the links, as well as the angle the coupler link makes with the horizontal, are chosen so that the instant center of the knee joint mechanism, when mounted in a prosthesis, will be above the level of the knee joint for up to 90° flexion, and the knee center at the stance position, and for about 20° of flexion from the stance position, will be behind the load line.

In yet another embodiment of the invention, a four-bar knee joint mechanism is provided wherein the dimensions of the coupler link, the anterior link, the fixed link and the posterior link, as well as the angle made by the coupler link with horizontal, are chosen to optimize the height of the instant center of the mechanism.

In another embodiment of the present invention, a four-bar knee joint mechanism is provided wherein the dimensions of the links, and the angle made by the coupler link with the horizonal, are chosen to optimize the height of the instant center of the mechanism, and to provide for flexion of up to 145°. This enables the amputee to kneel comfortably.

In another embodiment of the invention, an artificial leg comprising an upper leg stump or socket portion, and a lower or shin portion, is provided in which a substantially horizontal plate at the shin portion is connected to a rearwardly and upwardly sloped link at the base of the socket portion by an anterior and a posterior pair of pivoted links, wherein the instant center of the four-bar mechanism thus provided, for up to 90° of flexion, is always above that of the natural knee joint.

Therefore it is an object of the present invention to provide an improved knee disarticulation prosthesis.

A further object of the present invention is to provide an improved knee joint mechanism for use in knee disarticulation prosthesis.

A still further object of the present invention is to provide an improved four-bar knee joint mechanism wherein the height of the instant center of the mechanism is optimized.

A still further object of the present invention is to provide a four-bar knee joint mechanism having the maximum possible degree of flexion.

A still further object of the present invention is to provide an artificial leg having an improved knee joint mechanism wherein the height of the instant center above the normal knee joint is optimized and-the artificial leg has flexion of up to 145°.

Further objects and advantages of this invention will be apparent from the following description in appended claims, reference being made to the accompanying drawings forming a part of the specification, wherein like reference characters designate corresponding parts in the several views.

BRIEF DESCRIPTION OF THE DRAWINGS

FIG. 1 is a elevational view of a four-bar knee joint mechanism known in the prior art;

FIG. 1.1 shows a one gait cycle in normal human locomotion.

FIG. 1.2 shows a drop in knee level that occurs for a K/D amputee when fitted with the same knee joint as an A/K amputee.

FIG. 1.3 shows the downward shift of locus of knee centers that occurs for a K/D amputee when the same four-bar knee as for an A/K prosthesis is fitted.

FIG. 1.4 shows parameters for a four bar mechanism.

FIG. 1.5 shows attachment point geometry for the invention using a hydraulic unit.

FIG. 2.1 shows the variation of the instant center curve when the fixed link of the prior art mechanism of FIG. 1 was increased in length with the remaining links being unchanged.

FIG. 2.2 shows the change in instant centers when the posterior link of the prior art mechanism of FIG. 1 was lengthened, with the other lengths remaining constant.

FIG. 2.3 shows the change in instant centers when the coupler link of the prior art device of FIG. 1 was increased by a finite amount, with the remaining links unchanged.

FIG. 2.4 shows the change in instant centers when the anterior link of the prior art mechanism of FIG. 1 was lengthened a finite amount, with the remaining links unchanged.

FIG. 2.5 shows the change in instant centers when the angle of the coupler link of the prior art device of FIG. 1 was changed.

FIG. 2.6 shows the change in the instant center curves when the prior art mechanism of FIG. 1 was optimized.

FIG. 2.7 shows the difference in the height of the instant centers of the optimized device of FIG. 2.6 for degrees of knee flexion ranging between 0 and 90 degrees.

FIG. 3 is a perspective view of a construction embodying the present invention;

FIG. 9 is an elevational view of the construction shown in FIG. 3;

FIG. 10 is a partial sectional view, taken in the direction of the arrows along the section line 10—10 of FIG. 9;

FIG. 11 is a partial sectional view, taken in the direction of the arrows, along the section line 11—11 of FIG. 10;

FIGS. 12.1 through 12.3 are elevational views showing the construction of FIG. 3 in various positions of flexion.

FIG. 13 is an elevational view of a modification of the construction shown in FIG. 3.

FIGS. 16.1 through 16.3 are elevational views of the construction shown in FIG. 14 in various positions of flexion.

Figure 4:
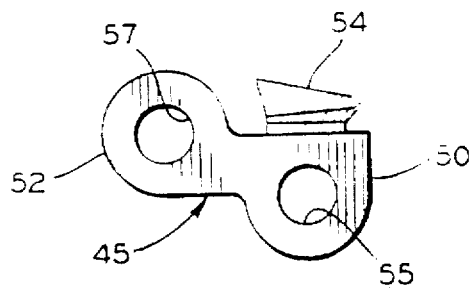
FIG. 4 is an elevational view of the coupler link shown in FIG. 3.

It is to be understood that the present invention is not limited in its application to the details of construction and arrangement of parts illustrated in the accompanying drawings, since the invention is capable of other embodiments, and of being practiced or carried out in various ways within the scope of the claims. Also, it is to be understood that the phraseology and terminology employed herein is for the purpose of description, and not of limitation.

DESCRIPTION OF THE PREFERRED EMBODIMENT

FIG. 1.2 shows the drop in the knee joint that occurs for a K/D amputee when fitted with the same knee joint as an A/K amputee.

FIG. 1.3 shows the downward shift of the locus of knee centers that occurs for a K/D amputee when the same four-bar knee as for an A/K prosthesis is fitted.

It can been seen that the path of the knee center when flexion approaches 90° will be below the normal path of the knee center for an A/K amputee (which, as stated above, closely approximates the normal knee) and this is what provides the problems of toe clearance and gait for the amputee.

Thus, improving the existing four-bar knee mechanisms so that the instant center of the knee joint for a K/D prosthesis would at least approximate the instant center available for the A/K prosthesis, i.e., approximate the normal knee center closely was the problem that needed to be solved in the art.

A review of the existing literature showed where the inventive effort should be directed. A variety of knee joint mechanisms are available. All of these are designed for A/K amputees and are used for A/K and K/D prosthesis. A review of manufacture's brochures (Blatchford Catalog 1992; Hosmer Dorrance Corporation, 1987; Mauch Laboratories, Inc. 1976–1988) does not indicate any designs made specifically for knee disarticulation amputees. The four and six-bar knee mechanisms shown therein are usually coupled with an adjustable hydraulic or pneumatic device (located in the shank) to exercise control over the swing phase of walking (Peizer and Gardner, 1972). Examples are the Henschke-Mauch S-N-S Knee, the Blatchford Pneumatic Knee, the U.S. M.C. Polycentric Knee and Ultra Roelite Knee.

In single axis knees, swing control is usually provided by mechanical friction applied about the axis of rotation. This mechanical system has the advantage of simplicity, but is functionally considered inferior to the new fluid control systems mentioned above. Examples of mechanical friction knees are the standard wood knee, the standard metal knee, the Teufel Secura Knee, the Blatchford BSK Knee and the Otto-Bock Single-Axis Knee.

The Dupaco Single-Axis Knee with hydraulic swing phase control has been used for K/D prosthesis (Hosmer, 1989). Using this single axis device has been shown to drop the knee joint level by nearly 3". For this reason it was not felt that any improvements in single axis devices could solve the problem in the art.

Since the four-bar mechanism is simpler and most cost effective when compared to six-bar mechanisms, and has better functionality when compared to a single-axis knee joint, it was decided that an improved four-bar mechanism held the best chance of solving the problem present in the art.

In a four-bar mechanism, the socket or thigh portion of the prosthesis forms the coupler, and the shank or shin portion of the prosthesis is the fixed link. The coupler and the fixed link are joined by anterior and posterior links. The intersection of a line drawn through the anterior and the posterior links is the instant center or knee center. If points are plotted from the extended (stance) position of the artificial leg or prosthesis as it is moved through various positions of flexion, a curve of instant centers is generated.

Radcliffe (1970) established the basic requirements for the knee mechanism for an A/K prosthesis. The amputee has to control the entire prosthesis by means of the residual stump housed in the socket of the prosthesis. In the stance, or fully extended position, it is necessary that the knee center or the instant center be located behind the load line (the line passing through the hip and the point of contact with the ground) for stability. Also if the knee center were located at a position well above, i.e. closer, to the hip joint when the knee is fully extended in the weight bearing phase, it would afford the amputee an ample mechanical advantage in order to initiate the swing phase. FIG. 1.3 shows that in the case of the K/D amputee, the knee centers using the current knee mechanisms fall below the level of the anatomical knee from flexion angles of about 45°. This causes toe clearance problems with the ground in the swing phase of the walking cycle. Also when the amputee has one normal limb, coordination problems result during the gait cycle because the knee levels do not match. Thus the study of the prior art further showed that the development of a new mechanism which would give a higher instant center at 90° flexion than provided by currently used mechanisms would solve the problems present in the prior art for K/D amputee prosthesis.

Provision of higher instant centers at 90° flexion also would result in raised instant centers in the swing phase of the walking cycle, thereby enabling a more natural gait with less effort by the hip flexor muscles. In order to achieve this, the variation of the form of the instant center curve was studied as the various parameters of the four-bar mechanism were varied. Graphical investigation was substantiated by mathematical formulations for the variations. Optimization methods were also used to validate the final design of the four-bar mechanism to be used for disarticulation amputees.

It was decided that the existing four-bar mechanism manufactured by Otto Bock of Minneapolis, Minn., and shown in FIG. 1, would be the starting point for our study, although any existing four-bar mechanism could have been used. FIG. 1.4 shows the parameters used in a study of the four-bar mechanism. The most important requirement for the improved four-bar mechanism is that the instant center (IC) curve of the mechanism should be such that the instant center at 90° flexion should be as close to the anatomical knee as possible.

The expressions for the coordinates of the instant center are derived in terms of the link parameters and the coupler input angles. Referring to FIG. 1.4, $L_1$ through $L_4$ are the link lengths, $\theta_2$ and $\theta_4$ are the angles made by $L_2$, (the posterior link) and $L_4$ (the anterior link) respectively with the horizontal, and $\theta_3$ is the coupler input angle. Parameter $\alpha$ is the angle made by the coupler with the horizontal in the initial or stance configuration. Parameters $L_c$ and $\theta_c$ define the location of a coupler point (CP). Since the fixed length will be assumed to be horizontal, as in most prior devices, the coordinates of the end points are given by (O,O) for point A, and ($L_1$, O) for point B. Using FIG. 1.4 and the appropriate mathematical equations and operations the coordinates of the instant center can be determined as $$Y_{IC} = \frac{L_1 \tan\theta_2 \tan\theta_4}{\tan\theta_4 - \tan\theta_2} \text{ and } X_{IC} = \frac{Y_{IC}}{\tan\theta_2}$$

$$Y_{IC} = \frac{L_1 \tan\theta_2 \tan\theta_4}{\tan\theta_4 - \tan\theta_2} \text{ and } X_{IC} = \frac{Y_{IC}}{\tan\theta_2}$$

The coordinates of the coupler point (CP) are given by $X_{CP} = X_C + L_C \cos\theta_C$ and $Y_{CP} = Y_C + L_C \sin\theta_C$.

Using the above equations, three approaches were used to develop the improved four-bar mechanism of the present invention. First an analytical analysis was performed to determine and show pictorially what the instant center curves looked like when the lengths of the various link and the coupler angle were varied. Secondly, a sensitivity analysis was performed which involved the derivation of the equations of change of the link dimensions and angles. This showed how the instant center height would increase or decrease with a change in dimension. For example, it was found that the instant center height would increase with a decrease in the coupler link length.

Thirdly, an optimization analysis was performed. Optimization is determining the maximum increase in the height of the instant center at 90° flexion subject to reasonable length limitations. The greatest increase in the height of the instant center at 90° flexion can be shown to correspond to the greatest increase in height of the instant center while the amputee is walking.

It was necessary to use reasonable length limitations in the analysis. While the instant center could still be higher if the coupler length were made less than 1", because of manufacturing and other design limitations, it is hard to make the coupler length less than 1" in length.

Analytical Analysis

FIG. 2.1 shows the variation of the instant center curve if links $L_2$ through $L_4$ were held constant and the length of link $L_1$ of the prior art four-bar linkage was increased by 0.2". FIG. 2—2 shows that at 90° flexion there was practically no change in the height of the instant centers.

A similar analysis was done with links L1, L3, and L4 being held constant, and with the length of L2 increased by 0.21". FIG. 2—2 shows that at 90° flexion, the instant center curve of the modified mechanism actually had a decrease in height of the instant center curve.

A similar result was reached with the variation of the instant center curve with link L3 being increased by 0.2", and the other links being held constant. FIG. 2-3 shows that, again, a decrease in the height of the instant center at 90° flexion was found.

Only when link L4 was increased in length by 0.2", and the rest of the links held constant, was an increase in height of the instant centers found, as shown in FIG. 2.4.

With the modifications in the lengths of the links not providing particularly satisfactory results, it was decided to try a change in the coupler angle as perhaps providing a bigger change in the instant center heights. As can be shown by FIG. 2.5 the change in the height of the instant center with the change in the coupler angle provided the greatest change.

Once it was learned that a change in the coupler angle along with a change in one of the links could produce the desired result, a sensitivity analysis was performed.

Sensitivity Analysis

As mentioned earlier, the coordinates of the instant center depend on the parameters defining the four-bar mechanism. The four-bar is a one degree of freedom system. Specifying one of the motion parameters will define the configuration at any instant. In order to determine the sensitivity of the Y coordinate of the instant center to changes in the mechanism parameters, $\partial Y_{IC}$ was determined in terms of variations in the independent parameters $\partial L_1$, $\partial L_2$, $\partial L_3$, $\partial L_4$ and $\partial\alpha$ and one dependent parameter (in this case, $\partial\theta_2$). The equation $A\sin\theta_2 + B\cos\theta_2 = C$ gives the dependence of variable $\eta_2$ on the parameters of the four-bar linkage that can be varied independently. Differentiating this equation and rearranging the terms gives, $$\partial\theta_2(2L_1L_2\sin\theta_2 - 2L_2L_3\sin\theta_2\cos(\alpha + \theta_3) + 2L_2L_3\cos\theta_2\sin(\alpha + \theta_3)) =$$

$$(-2L_1 + 2L_2\cos\theta_2 + 2L_3\cos(\alpha + \theta_3))\partial L_1 +$$

$$(-2L_2 - 2L_3\cos\theta_2\cos(\alpha + \theta_3) + 2L_1\cos\theta_2 - 2L_3\sin\theta_2\sin(\alpha + \theta_3))\partial L_2 +$$

$$(-2L_3 - 2L_2\cos\theta_2\cos(\alpha + \theta_3) -)$$

$$2L_2\sin\theta_2\sin(\alpha + \theta_3) + 2L_1\cos(\alpha + \theta_3))\partial L_3 + (2L_4)\partial L_4 +$$

$$(2L_2L_3\cos\theta_2\sin(\alpha + \theta_3) - 2L_2L_3\sin\theta_2\cos(\alpha + \theta_3) - 2L_1L_3\sin(\alpha + \theta_3))\partial\alpha$$

The coordinates of point D on diagram 4 can be expressed as $X_D = L_2 \cos\theta_2 + L_3 \cos(\alpha+\theta_3)$, and $Y_D = L_2 \sin\theta_2 + L_3 \sin(\alpha+\theta_3)$. The coordinates of point D can also be expressed in another form as $X_D = L_1 + L_4 \cos\theta_4$ and $Y_D = L_4 \sin\theta_4$. Equating the two forms for the X and Y coordinates of point D and simplifying we get $L_4 \cos\theta_4 = L_2\cos\theta_2 + L_3 \cos(\alpha+\theta_3) - L_1$ and $L_4 \sin\theta_4 = L_2 \sin\theta_2 + L_3 \sin(\alpha+\theta_3)$. Dividing these last two equations, we get the expression for $\tan\theta_4$ in terms of $\theta_2$ and the other independent parameters. Substituting this expression into equations above for the X and Y coordinates of the instant centers, we get the final expressions for the variation in $Y_{IC}$ as follows:

$$\partial Y_{IC}(L_3\sin(\alpha + \theta_3) - L_3\tan\theta_2\cos(\alpha + \theta_3) + L_1\tan\theta_2) =$$

$$(-Y_{IC}\tan\theta_2 + L_2\tan\theta_2\sin\theta_2 + L_3\tan\theta_2\sin(\alpha + \theta_3))\partial L_1 +$$

$$(L_1\tan\theta_2\sin\theta_2)\partial L_2 +$$

$$(-Y_{IC}\sin(\alpha + \theta_3) + Y_{IC}\tan\theta_2\cos(\alpha + \theta_3) + L_1\tan\theta_2\sin(\alpha + \theta_3))\partial L_3 +$$

$$(-Y_{IC}L_3\cos(\alpha + \theta_3) - Y_{IC}L_3\tan\theta_2\sin(\alpha + \theta_3) +$$

$$L_1L_3\tan\theta_2\cos(\alpha + \theta_3))\partial\alpha +$$

$$(Y_{IC}L_3\sec^2\theta_2\cos(\alpha + \theta_3) - Y_{IC}L_1\sec^2\theta_2 + L_1L_2\sec^2\theta_2\sin\theta_2 +$$

$$L_1L_2\tan\theta_2\cos\theta_2 + L_1L_3\sec^2\theta_2\sin(\alpha + \theta_3))\partial\theta_2$$

These equations were incorporated into a computer program and with the parameters of the existing mechanism as the basis, the deviation in the Y coordinate of the IC was determined for changes in the various parameters. The mathematically predicted changes from the above formulations were compared with the actual change in the $Y_{IC}$ at the various coupler rotation between the existing mechanism and the mechanism created by the changed parameters and were found to be in close agreement. Thus the sensitivity of the Y coordinate of the IC to changes in the various parameters of the four-bar mechanism was quantified.

Optimization

The OPT3 program by Gabriele and Beltracchi, published in 1991, is a well-known optimization package and was used to determine the mechanism with the highest instant center at 90 degrees flexion. The function to be maximized was the difference between the Y coordinate of the instant center at 90 degrees flexion and the corresponding value for the existing mechanism we were using for the start of our analysis. Initially, upper and lower limits were set for the lengths and the coupler angle in the initial configuration. One constraint incorporated in the formulation was the Grashof criterion so that the objective function was evaluated only for feasible mechanisms. The other constraint was that the width (front to back) of the mechanism in the initial configuration should be less than or equal to 3.2 inches so that the mechanism is cosmetically acceptable. It can be understood by those skilled in the art that each particular application may have different initial constraints.

Initially, the problem was formulated with reasonable upper and lower limits for the lengths $L_1$ through $L_4$ and the coupler angle. This gives a five variable problem. However, this resulted in convergence to solutions which were strongly dependent on the variable limits. Also, the solution obtained by optimization often yielded a lower or poorer value of the instant center at 90 degrees flexion than some solutions obtained from the above graphical analysis, even though the link lengths corresponding to the better solution lay within the bounds specified in the optimization formulation. This occurred because monotonic increase or decrease of the objective function is very common in these types of problems. Therefore, finding a maximum or minimum without settling onto either upper or lower bounds of the five variables was difficult. Therefore, the number of variables was reduced by assigning values to some of the variables. The previous graphical analysis proved to be useful in determining which of the variables could be assigned values. From the graphical analysis it was evident that the effects of changes in $\alpha$, $L_1$, and $L_3$ were independent of changes in other combinations of variables. Thus, suitable values that would be favorable to increasing the instant center at 90 degrees flexion were assigned to these three variables and $L_2$ and $L_4$ were now the only remaining variables. These were expressed as multiples of $L_1$.

The second problem was the non-closure problem of the linkage for a particular set of dimensions. In this case the objective function could not be evaluated causing no new value to be assigned to the objective function. In the iterative of process, if the value of the objective function does not change during several consecutive iterations, the program stops, saying an optimum has been found. In order to eliminate this problem the Grashof criterion was incorporated as a constraint to ensure that the objective function was evaluated only for feasible mechanisms.

Once the above problems were tackled the optimization program was run, and the final solution found. The solution was verified by specifying different starting points to the algorithms, and it was found that it always converged to the same solution. The optimization yielded a design that raises the Y coordinate of the instant center at 90 degrees flexion by 1.09 inches. The dimensions of the four bar linkages which achieves this are $L_1$ equals 2.5 inches, $L_2$ equals 3.575 inches, $L_3$ equals 1.0 inches, $L_4$ equals 3.75 inches and the initial coupler angle, $\alpha$, equals $-25$ degrees.

A plot of the height of the instant center above the base link versus degrees of flexion is shown in FIG. 2.7. It can be seen that the optimized mechanism initially provides a lower instant center than the prior art device. However, it can be seen that once the degree of flexion exceeds approximately 18 degrees, the optimized mechanism consistently has a higher instant center than the prior art mechanism. Once the straight line, or center-to-center, distances for the optimized mechanism were obtained the improved four-bar mechanism could be produced.

Various factors needed to be considered in making a working model with the linkage dimensions obtained from the kinematic design. Strength considerations required the links to be a reasonable thickness and width. Weight considerations need to be taken into account so that the wearer of the prosthesis did not find the device to be a significant added burden to carry. Link interferences had to be identified and eliminated. The finished device is also preferably easy to machine, have standard modes of attachment to properly affix to the socket and shank, enable easy assembly and disassembly and be cosmetically acceptable.

Also of primary importance are the safety and functionality of the device. The prototype was developed using an entire prosthesis consisting of a socket, a foot shank assembly, and the prior art four bar knee with an accommodated hydraulic unit. Using appropriate modelling techniques well known in the art, a first embodiment of the invention was developed. It is shown in FIG. 3–7.

Referring now to FIG. 3, there is shown a prosthesis generally indicated by the numeral 40 embodying the construction of the present invention. The prosthesis includes a stump or knee block 41 and a knee shin or shin 42. The stump 41 and shin 42 are indicated in phantom lines to indicate that the improved four bar mechanism of the present invention is usable with a wide variety of existing stumps and shins made by existing prosthesis manufacturers and as such form no part of the present invention except in combination with the improved four bar mechanism generally indicated by the numeral 43, or as discussed below in connection with FIGS. 14–18. The four bar mechanism 43 generally includes a fixed link 44, a coupler link 45, one or more anterior links 46, and one or more posterior links 47.

Referring now to FIG. 4 the coupler link 45 can be seen in more detail. The coupler link has an anterior portion 50 having an anterior coupler bearing 55 formed therein. A shank 54 is formed proximate the top of the anterior portion of coupler link 45. The semi-circular mounting shank can be used, as well as any other shank shape such as, but not limited to, the square shank shown on the coupler in FIG. 14.

The posterior portion 52 of coupler link 45 has a posterior coupler bearing 57 formed therein.

Figure 5:
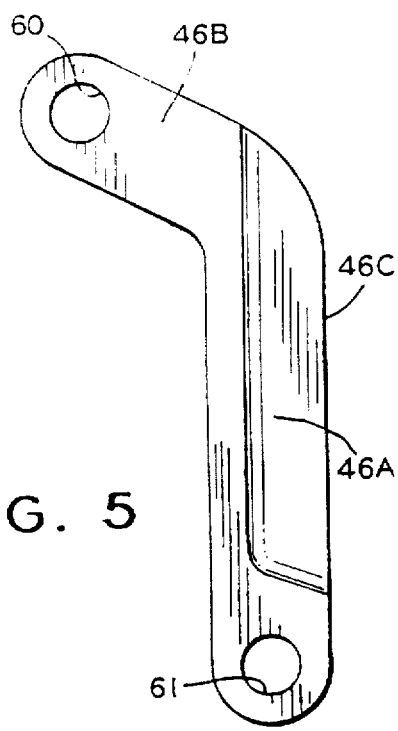
FIG. 5 is an elevational view of one of the anterior links shown in FIG. 3.

Referring now to FIG. 5 the four bar mechanism 45 of the present invention includes a pair of anterior links 46 each having a straight portion 46A and a angled portion 46B for purposes that will be described hereinafter. A first opening or bearing 60 of the anterior link 46 is provided in the angled portion 46B, and a second opening or bearing 61 of the anterior link 46 is provided in the straight portion 46A. The center to center distance, or straight line distance, between the first bearing 60 and the second bearing 61 is the optimized or substantially optimized distance determined earlier. A relief portion 46C is provided substantially in the straight portion 46A to provide for weight saving of the mechanism. In the mechanism shown, two anterior links 46 are needed.

Figure 6:
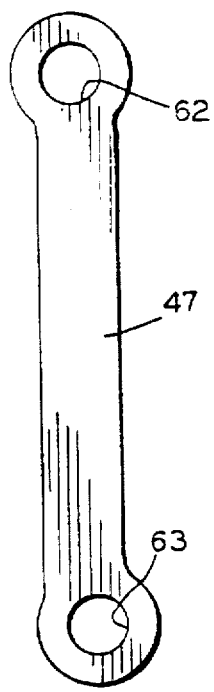
FIG. 6 is an elevational view of one of the posterior links shown in FIG. 3.

Referring now to FIG. 6, there is shown one of a pair of straight posterior links 47. In a manner similar to the anterior links 46, a first opening or bearing 62 is provided proximate one end of the straight posterior link 47 and a second opening or bearing 63 is provided proximate the other end of the posterior link 67. The center to center distances or straight line distances between the first opening or bearing 62 and the second opening or bearing 63 are again the center to center or straight line distances determined earlier. The shape of the posterior links may vary, as will be described later, in order to provide the necessary clearance for efficient operation for the mechanism.

Figure 8:
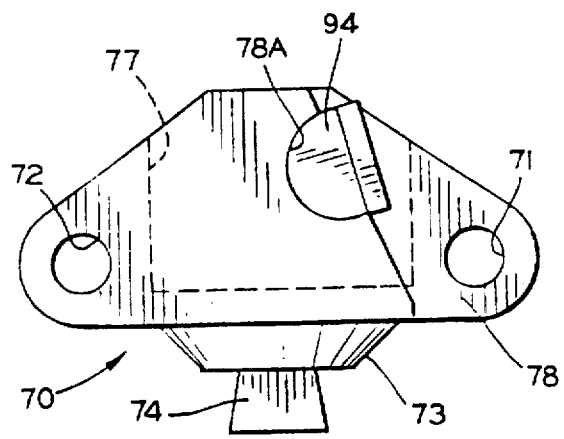
FIGS. 8 is a plain view of the construction shown in FIG. 7.
Figure 7:
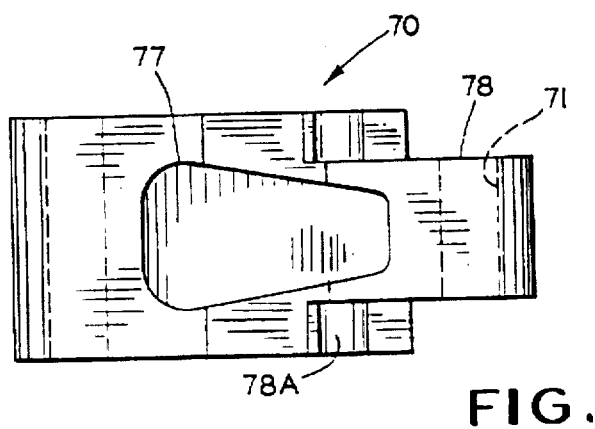
FIG. 7 is an elevational view of the fixed or base link shown in FIG. 3.

Referring now to FIGS. 7–8, the base link is shown. The fixed or base link 70 has an anterior base bearing 71 and a posterior base bearing 72. Proximate the lower or bottom portion of the base link 70 is provided a platform portion 73 having a shank 74 affixed thereto. As shown in FIG. 8 the shank 74 fits into a recess 75 in the shin portion 42 of the prosthesis and is held therein by set screws 77. A void 77 is provided in the body of the base link 70 for weight saving purposes.

A lug portion 78 of the base link 70 contains the anterior base bearing 72. The lug portion 78 further includes a recess portion 78A for purposes to be described below.

Referring to FIGS. 9–11, a friction means 80 is shown interposed between the straight posterior links 47 and the base link 44. If friction means 80 are to be provided, the posterior base bearing 72 of the base link 70 may be made somewhat larger than the anterior base bearing 72. A pair of liners 81, which may be of a suitable material such as nylon, are provided. Diameter reducing means such as indicated by the slit portion 82, are shown. A first posterior shaft 83 is placed through the liners 81. Pressure can be applied to the liners 81 by pressure application screws 85. A notch 86 is provided proximate each end of the base posterior shaft 84. A plate 87 is attached to the outside of each of the posterior links 47 by fastening means, such as screws 88. The plates 87 fit into the notches 86. It can be seen that the plates 87 thus force the base posterior shaft 84 to rotate with the posterior link 47. The base posterior shaft 84 is, thus, subject to the friction applied to the posterior shaft 84 by the liners 81. The other pins or shafts, i.e. the base anterior shaft 90, the posterior coupler shaft 58, and the anterior coupler shaft 56, are preferably the same size as base posterior shaft 84 but do not have friction means applied thereto. Thus, the base anterior bearing 71, as well as the second anterior bearing 61 of each anterior link 46 are sized to provide a rotating fit with the base link anterior shaft 90. In a similar fashion, the anterior coupler shaft 56, as well as the first opening bearings 60 of the anterior link 46, are sized for a rotating fit. The posterior coupler shaft 58 is sized for a rotating fit with first bearing 62 of straight link 47.

In the assembled condition of the four bar linkage 43 shown in FIGS. 3 and 8 it can be seen that the anterior coupler shaft 56, posterior coupler shaft 58 and base link anterior shaft 90 are all restrained from lateral movement by C-washers 91.

FIG. 8 shows the improved four bar mechanism 43 in a position of 0° flexion. To provide for quiet operation of the mechanism a bumper 94 is provided in the recess 78A of the fixed link 78 and bears against the anterior links 46 in the 0° of flexion position.

The positions of the various bars of the improved four bar linkage are shown in FIGS. 12.1 through 12.3 for various degrees of flexion between 0° and approximately 110° flexion, which is the maximum obtainable with this modification of the invention. FIG. 12.1 shows 45° of flexion, FIG. 12.2 shows 90° of flexion and FIG. 12.3 shows 110° degrees of flexion.

Referring to FIG. 13 there is shown a modification of the present invention wherein the four bar linkage 43 previously described is fitted with a hydraulic cylinder 99 for improved swing control. All of the portions of the linkage of FIG. 13 are identical to that shown in FIG. 3, except the straight posterior links 47 are now ternary (three points of connection) links instead of the binary (two points of connection) links previously shown.

In this modification of the invention, each of a pair of posterior links 47 has a shaft bearing 95 provided therein through which is passed a shaft pin 96 which may be restrained in any appropriate manner such as by the C-washers 91 previously described. Provided in the base link 44 are a pair of cylinder bearings 97 which may hold a cylinder connecting pin 98. Any of the well known swing control hydraulic cylinders, such as those manufactured by Mauch Laboratories, Inc. under model number 00100, or others, may be mounted to the improved four bar mechanism disclosed. The cylinder 99 would be attached to the base link 44 by means of the cylinder connecting pins 98 and the shaft 100 would likewise would be rotatably connected to the shaft pin 96 which is contained by the shaft bearing 95. This will provide improved swing control in the improved four bar mechanism of the present invention.

While the modification of the invention shown in FIG. 13 is satisfactory for many purposes, it does not provide for much protection for the hydraulic unit, nor does it provide for the use of the latest type of hydraulic units such as the Mauch Microlite Hydraulik Swing Control Unit, which provides independently adjustable resistances to extension and flexion which closely duplicate the forces of the leg muscles in action during the swing phase of the gait cycle.

Figures 14, 15:
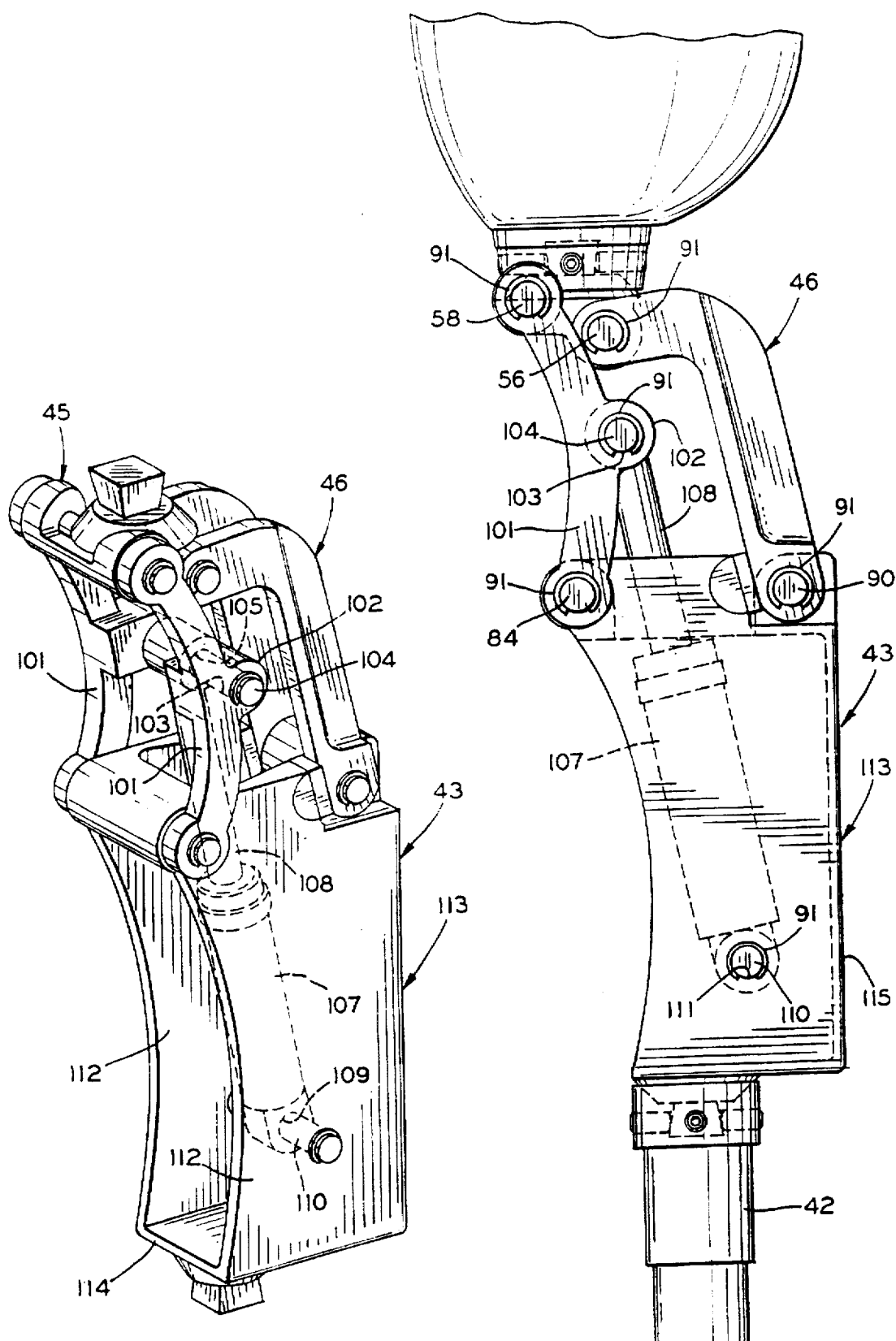
FIG. 14 is a perspective view of a further modification of the constructions shown in FIG. 3 having a hydraulic swing control unit.
FIG. 15 is an elevational view of the construction shown in FIG. 14.

When using a hydraulic unit having such independently adjustable resistances, the mounting of the unit becomes somewhat critical, and this necessitated the design of the modification of the invention shown in FIGS. 14 and 15. In this modification, the fixed or base link 44 takes the form of a hollow frame 113 which provides for the protection of the hydraulic unit 107 and the necessary mounting geometry for the cylinder. The attachment point geometry for a hydraulic unit in a four bar mechanism can be seen from diagram 5 immediately below. Referring to FIG. 1.5, the coordinates $x_1 y_1$ represent the proximal point of attachment of attachment of the hydraulic unit at 0° flexion, i.e. in the stance phase.

At 90° flexion, this point moves to point 2 (coordinates $x_2 y_2$). With reference to link 2, the point of attachment can be defined by length D at angle $\partial$. It is known that for the Microlite cylinder fitted to a single axis knee, that at 90° flexion the unit is vertical, with the moving attachment point having undergone a displacement of 1.18 inches horizontally and 1.18 inches vertically downwards during the course of movement from 0° flexion to 90° flexion. Knowing this, the maximum compression that such cylinder undergoes is 1.29 inches, and it is desired when fitting the mechanism to a four bar knee to achieve approximately the same compression. A similar analysis would be made with other manufacturer's units.

With reference to link 2, the point of attachment can be defined by length D at angle $\partial$. The coordinates of this point on link 2 are then given by $D\cos(\theta_2-\partial)$, $D\sin(\theta_2-\partial)$. Using the foregoing information the parameters D and $\partial$ are determined using the equations $X_2-X_1=1.18$ and $Y_2-Y_1=1.18$.

For the four bar knee mechanism the coupler is vertical at 115° rotation of the mechanism because the angle made by the coupler in the initial configuration corresponding to 0° is −25°. The analysis shows that $\theta_2=98.7°$ at $\theta_3=0°$ and $\theta_2=50.2°$ at $\theta_3=90°$. Therefore, in terms of D and $\partial$, the previous equations become Dcos $(50.2−\partial)$−Dcos $(98.7−\partial)=$ 1.18 and Dsin $(98.7−\partial)$−Dsin $(50.2−\partial)=1.18$. Since these equations have equivalent values, this can be simplified to cos $(50.2−\partial)$−cos $(98.7−\partial)=$sin $(98.7−\partial)$−sin $(50.2−\partial)$. Using the appropriate trigometric identities in solving for $\partial$, we have $\partial=29.45°$. Choosing $\partial=30°$ the value of D=2.051 inches is obtained from one of the above equations, and the value of D=2.012 inches is obtained from the other equation. The lower value (2.012 inches) obtained from the equation for vertical displacement is chosen because it ensures that the hydraulic unit will not undergo a greater compression than what is was designed for. Thus the proximal point of attachment of the hydraulic unit is defined by the parameters D=2.012 inches at an angle $\partial=30°$ from the axis of link 2 with respect to FIG. 1.5. The coordinates of the distal point of attachment of the frame then are given by $x=x_2$ and $y=y_2−5.10$ where 5.10 is the length of the hydraulic unit 107 at 90° flexion. Knowing this, the point of attachment to the frame can be determined.

The coupler link 45, as well as the anterior links 46, in this modification of the invention are identical to those embodiments previously described and need not be discussed in detail herein.

The curved posterior link, for the purposes of clarity and understanding, will now be identified by the numeral 101 and the fixed or base link or frame is now identified by the numeral 113.

Because the hydraulic unit 107 is used to provide resistance, the friction means discussed above in relation to FIGS. 9–11 is not used, and thus the base posterior shaft 84 shown in FIG. 12 may be the same size as the base anterior shaft 90, the anterior coupler shaft 56 and the posterior coupler shaft 58. As before, C-washers 91 are used to hold the shafts in position. In this modification, however, the straight posterior links 47 have been replaced by curved posterior links 101. The center to center distances between the openings or bearing surfaces of the curved posterior links 101 are identical to those of the straight posterior links 47. However in this case the tongue portion 102 of the curved posterior link 101 has provided therein a cylinder shaft bearing or opening 103. A cylinder shaft mounting pin 104 having its ends mounted in the cylinder shaft bearings 103 and the shaft bearing 106 of the hydraulic unit 107 provides the mounting for the cylinder shaft 108. This provides the proximal mounting point for the hydraulic cylinder 107.

The distal mounting point is provided on the fixed link 43, which now takes the shape of a hollow frame 113, which surrounds the hydraulic cylinder on three sides to provide protection therefore, and provides ample opportunity to mount the hydraulic unit 107 by way of the cylinder bearing portion 109. A cylinder connecting pin 110 passes through the cylinder bearing 109, and connecting pin or bearings 111 provided in sidewalls 112 of hollow frame member 113. Because of the expansive sidewalls 112, the proper distal mounting point for a wide variety of hydraulic units 107 may easily be provided.

The hollow frame member 113, in addition to the side walls 112, has a bottom wall 114 and a front wall 115. As before, set screws 74 fit into a recess in the shin 73 to fasten the frame member 113 to the shin 42. By providing curved posterior links 101, approximately 120° of flexion is provided. The curved links 101 provide additional clearance from the stump 41 without adjusting the coupler link forward, as shown in FIGS. 12 and 12.2, or cutting away part of the stump as shown in FIG. 12.3. This can be seen by referring to FIGS. 16.1 through 16.3. Whether the linkage is curved or straight makes no difference for flexion up to 90° as shown by FIGS. 16.1 and 16.2. However, once past this, to avoid interference the curved link gives an approximate 10° increase in flexion, which is significant.

Figure 17:
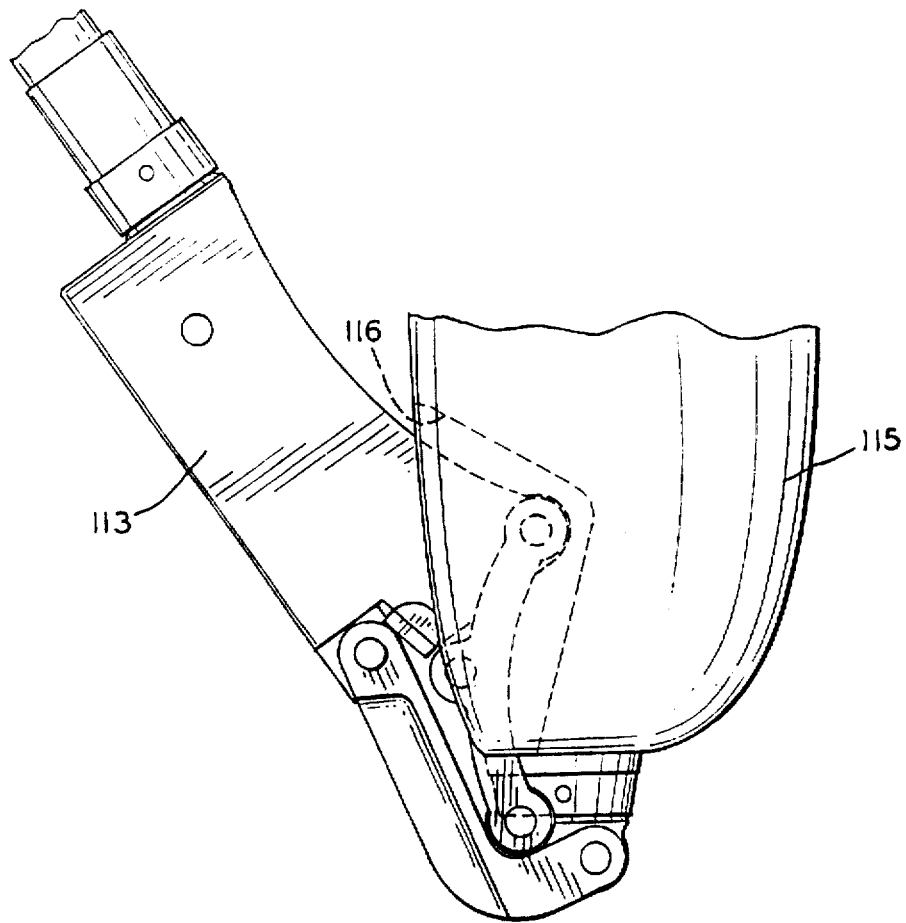
FIG. 17 is an elevational view of a modification of the construction shown in FIG. 15 modified to provide 145° of flexion, by providing a recess in the stump.
Figure 19:
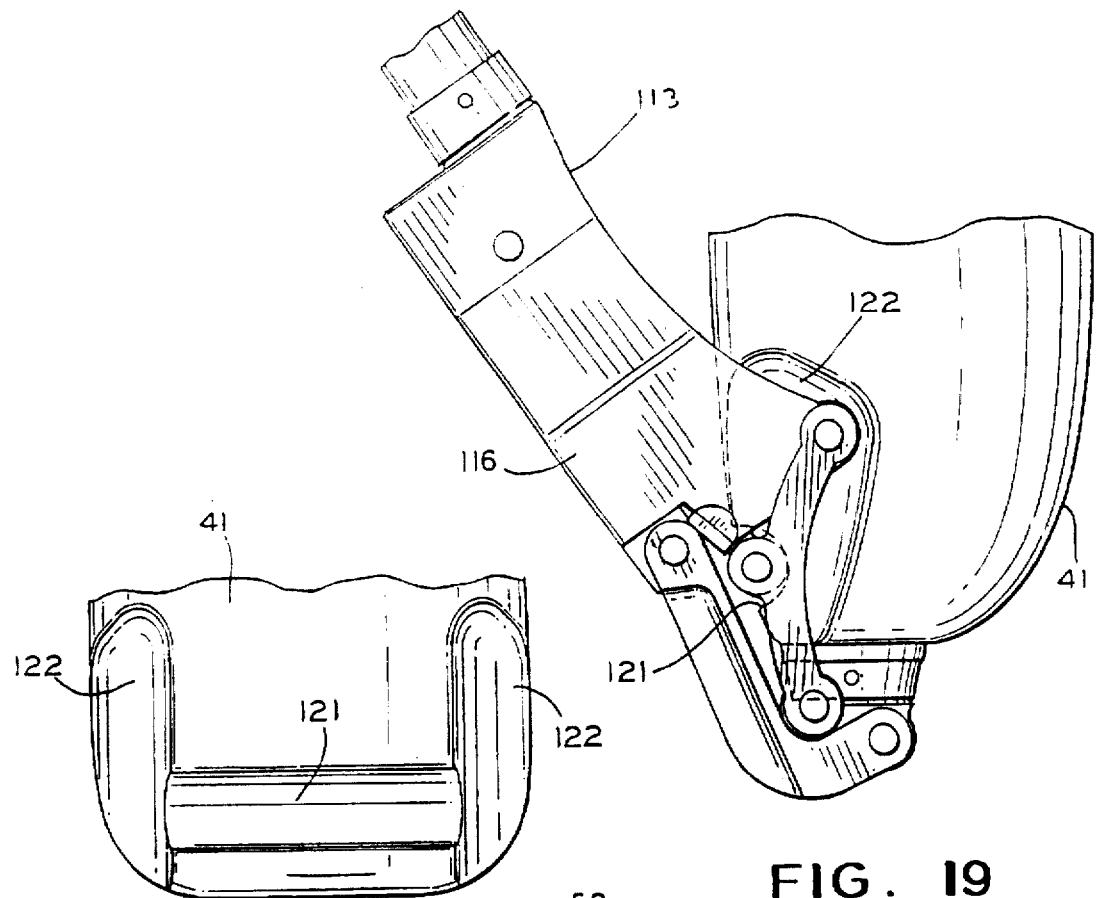
FIG. 19 is an elevational view of the construction shown in FIG. 18.
Figure 18:
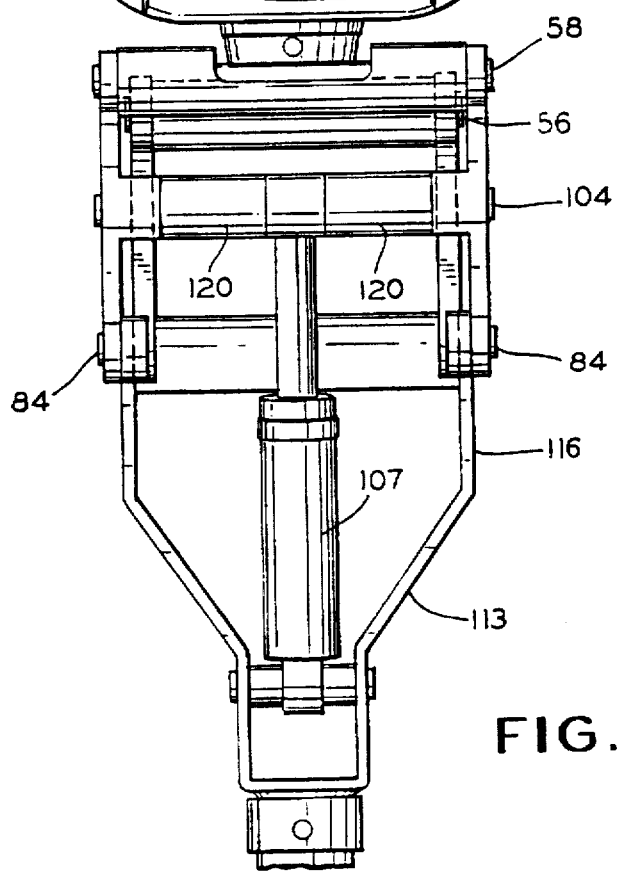
FIG. 18 is an end view of a further modification of the construction shown in FIG. 15 wherein additional flexion is obtained by widening a portion of the four-bar mechanism.

Referring now to FIG. 17, a further modification of the present invention is shown where the improved four bar mechanism 43 of the present invention having the curved posterior links 101 is combined with a modified stump 115 having recess 116 therein. It can be seen in this modification that the full 145° flexion is permissible because the entire hollow frame 113 fits within the recess 116. The use of the modified stump 115 will depend on the shape of the remaining condyle of the amputee. It is contemplated that for some amputees, this modification of the invention will not be usable.

Where the modification of the invention shown in FIG. 17 is not usable to achieve the full 145° flexion, the modification shown in FIGS. 18 and 19 may be used. In this case, the hollow frame member 113 forming the base or fixed link 44 has a widened upper portion 116 with correspondingly lengthened anterior coupler bearing 55, posterior coupler bearing 58, base posterior shaft 84 and base anterior shaft 90. Likewise, spacers 120 are provided on the extended cylinder shaft mounting pin 104. With the widened portion 116 of the hollow frame 113, the modifications to stump 41 take the form of horizontal recess 120 and vertical recesses 121 into which the widened mechanism fits. It should also be noted that in this modification, the base posterior shaft 84 is split into two very short portions with suitable retaining means so that the posterior portion of the hollow frame 113 can fit into the vertical recesses 121. With these modifications, a full 145° of flexion is possible as shown by the elevational view in FIG. 19.

By carefully studying the available prior art prostheses and the problems associated with using prior art prostheses on below knee amputations, a novel and improved four bar mechanism with an optimized instant center is provided which provides for an instant center near the anatomical knee center for flexion up to 90° and which can be used in the prosthesis to provide up to 145° of flexion.

What is claimed is:

1. In a knee joint for knee disarticulation prosthesis rotatable between flexed and extended positions, and comprising a four bar linkage consisting of a thigh link and a shin link pivotally connected to an anterior link and a posterior link to define a four bar linkage, the improvement comprising:

(a) the thigh link forming a negative angle with respect to a horizontal plane when the knee joint is in an extended position;

(b) the shin link being positioned substantially along the horizontal plane when the knee joint is in the extended position, the length of said shin link and said anterior link and posterior link, as well as the angle which the thigh link forms with respect to the horizontal plane, are selected to maximize a height, $Y_{IC}$, of an instant center of the knee joint for knee disarticulation prosthesis above the shin link at 90° flexion according to the equation:

$$Y_{1C} = \frac{L_1 \tan\theta_2 \tan\theta_4}{\tan\theta_4 - \tan\theta_2}$$

where $L_1$ is the length of the shin link, $\theta_2$ is the angle made between the posterior link and the shin link, and $\theta_4$ is the angle made between the anterior link and the shin link.

2. The device defined in claim 1, wherein mechanical friction means are imposed between the shin link and the posterior link.

3. The device defined in claim 1, wherein said anterior link comprises a pair of anterior links, each such anterior link having, (a) straight portion, (b) an angled portion, (c) a first bearing in the angled portion and (d) a second bearing in the straight portion, the center to center distances between the first bearing and second bearing substantially optimized.

4. The device defined in claim 3, wherein said posterior link comprises a pair of posterior links having (a) a first bearing at one extremity thereof and (b) a second bearing at the opposite end thereof, the center to center distances between the first bearing and the second bearing being substantially optimized.

5. The device defined in claim 4, wherein said shin link includes (a) a posterior base bearing, (b) an anterior base bearing, (c) a lug portion including a recessed portion, and (d) an axially extending void.

6. A four-bar knee joint mechanism including:

(a) a coupler link forming a negative angle of about 25° with the horizontal when said knee joint mechanism is in its stance position, said coupler link being no less than substantially one inch in length;

(b) an anterior link of approximately 3.75 inches in length between centers;

(c) a fixed link of approximately 2.50 inches in length between centers and in a horizontal position when said knee joint mechanism is in the stance position; and (d) a posterior link of approximately 3.575 inches in length between centers.

7. The device defined in claim 6, wherein mechanical friction means are imposed between the posterior link and the fixed link.

8. The device defined in claim 6, wherein said anterior link comprises a pair of anterior links, each such anterior link having, (a) straight portion, (b) an angled portion, (c) a first bearing in the angled portion and (d) a second bearing in the extremity of the straight portion, the center to center distances between the first bearing and second bearing being substantially optimized.

9. The device defined in claim 8, wherein said posterior link comprises a pair of posterior links having (a) a first bearing at one extremity thereof and (b) a second bearing at the opposite end thereof, the center to center distances between the first bearing and the second surface being substantially optimized.

10. The device defined in claim 9, wherein said fixed link includes (a) a posterior base bearing, (b) an anterior base bearing, (c) a lug portion including a recessed portion, and (d) an axially extending void.

11. The device defined in claim 6, wherein said posterior link includes a pair of curved posterior links, each having a tongue portion, each of said posterior links including a first bearing at one extremity of said link, a second bearing at the other extremity of said link, and a cylinder shaft bearing formed in said tongue portion of said curved posterior link.

12. The device defined in claim 11, wherein said fixed link includes a hollow frame member having a pair of opposed side walls, a front wall, a bottom wall, a pair of posterior base bearings and a pair of anterior base bearings.

13. The device defined in claim 12, and further including a connecting pin bearing formed in each of said side walls in a 180° opposed relationship.

14. The device defined in claim 13, and including a connecting pin mounted in said connecting pin bearings.

15. The device defined in claim 14, wherein a hydraulic cylinder is connected to said connecting pin bearings by said connecting pin, said hydraulic cylinder including a shaft and a shaft bearing, said shaft bearing rotatably connected to a cylinder mounting pin, said cylinder mounting pin rotatably connected to a cylinder shaft mounting pin rotatably connected to said cylinder shaft bearing formed in said tongue portion of said posterior links.

16. The device defined in claim 15, wherein the top portion of said hollow frame member is widened.

17. The device defined in claim 16, wherein a stump is mounted to said coupler link, said stump having recesses therein to accepted a portion of said hollow frame member and provide for 145° flexion.

18. A four-bar knee joint mechanism for knee disarticulation prosthesis, comprising:

a pair of anterior links;

a pair of posterior links;

a coupler link being pivotally connected to each pair of said anterior links and said posterior links;

a fixed link being pivotally connected to each pair of said anterior links and said posterior links;

a ratio of a length of said coupler link, a length of said fixed link, a length of each of said pair of anterior links, and a length of each of said pair of posterior links is 1:2.5: 3.75: 3.575.

19. The mechanism according to claim 18, further comprising a friction means interposed between said pair of posterior links and said fixed link.

20. The mechanism according to claim 18, further comprising a hydraulic means interposed between said pair of posterior links and said fixed link.

21. The mechanism according to claim 18, wherein each anterior link comprises an angled portion including a first bearing and a straight portion including a second bearing.

22. The mechanism according to claim 18, wherein each posterior link includes a first bearing at one end thereof and a second bearing at an opposite end thereof.

23. The mechanism according to claim 18, wherein said fixed link comprises a posterior base bearing, an anterior base bearing, a lug portion including a recessed portion and an axially extending void.

24. The mechanism according to claim 18, wherein the length of said coupler link is not less than one inch.

* * * * *